(12) United States Patent
Jester et al.

(10) Patent No.: US 9,817,945 B2
(45) Date of Patent: Nov. 14, 2017

(54) SYSTEMS AND METHODS TO OPTIMIZE RADIOLOGY EXAM DISTRIBUTION

(71) Applicant: General Electric Company, Schenectady, NY (US)

(72) Inventors: Eric Jester, Hoffman Estates, IL (US); Arun Viswanath, Lake Zurich, IL (US); Madhu Seepani, Lake In The Hills, IL (US); Shaoyu Feigler, Barrington, IL (US); Jeff Chu, Buffalo Grove, IL (US); Jiaohuan Wang, Schaumburg, IL (US); Vineet Ahuja, Palatine, IL (US); Charlotte Mae Shelton, Gilbert, AZ (US); Rhonda Eckstein, Baileyton, AL (US)

(73) Assignee: General Electric Company, Schenectady, NY (US)

( * ) Notice: Subject to any disclaimer, the term of this patent is extended or adjusted under 35 U.S.C. 154(b) by 229 days.

(21) Appl. No.: 14/091,801

(22) Filed: Nov. 27, 2013

(65) Prior Publication Data
US 2015/0149192 A1    May 28, 2015

(51) Int. Cl.
G06Q 10/00    (2012.01)
G06Q 50/00    (2012.01)
G06F 19/00    (2011.01)

(52) U.S. Cl.
CPC .......... *G06F 19/327* (2013.01); *G06F 19/321* (2013.01)

(58) Field of Classification Search
CPC ..... G06F 19/327; G06F 19/322; G06F 19/321
See application file for complete search history.

(56) References Cited

U.S. PATENT DOCUMENTS 7,970,634 B2 * 6/2011 Backhaus ............. G06F 19/327
                                                                   705/3
9,558,323 B2    1/2017 Jester et al.
(Continued)

OTHER PUBLICATIONS

United States Patent and Trademark Office, "Non-Final Office Action," issued in connection with U.S. Appl. No. 14/091,769 dated Aug. 31, 2015, 23 pages.

(Continued)

*Primary Examiner* — Michelle L Le
(74) *Attorney, Agent, or Firm* — Hanley, Flight & Zimmerman, LLC

(57) ABSTRACT

Example methods, systems, and computer readable media are disclosed to allocate a medical exam. An example method includes identifying an exam characteristic associated with the medical exam. The example method includes determining a plurality of allocation scores for a plurality of radiologists by comparing the exam characteristic to a radiologist characteristic for each of the plurality of radiologists. The example method includes determining one of the plurality of allocation scores with a highest value. The example method includes allocating the medical exam to one of the plurality of radiologists associated with the one of the plurality of allocation scores with the highest value. The example method includes marking the medical exam as allocated to the one of the plurality of radiologists associated with the one of the plurality of allocation scores with the highest value. The example method includes providing an indication that the medical exam is allocated via a graphical user interface.

21 Claims, 13 Drawing Sheets

(56) References Cited

U.S. PATENT DOCUMENTS

| | | | |
|---|---|---|---|
| 2003/0149598 | A1 | 8/2003 | Santoso et al. |
| 2004/0019501 | A1 | 1/2004 | White et al. |
| 2004/0249676 | A1* | 12/2004 | Marshall ............... G06F 19/327 705/2 |
| 2006/0053035 | A1 | 3/2006 | Eisenberg |
| 2006/0143060 | A1 | 6/2006 | Conry et al. |
| 2006/0195339 | A1 | 8/2006 | Backhaus et al. |
| 2006/0212317 | A1 | 9/2006 | Hahn et al. |
| 2007/0073556 | A1 | 3/2007 | Lau et al. |
| 2007/0143136 | A1 | 6/2007 | Moore, III et al. |
| 2007/0179831 | A1 | 8/2007 | Patnaik et al. |
| 2007/0226008 | A1* | 9/2007 | Halsted .................. G06Q 50/22 705/2 |
| 2009/0240529 | A1* | 9/2009 | Chess ................... G06F 19/328 705/3 |
| 2009/0287500 | A1 | 11/2009 | Benjamin et al. |
| 2009/0313046 | A1 | 12/2009 | Badgett et al. |
| 2011/0066449 | A1 | 3/2011 | Backhaus et al. |
| 2011/0113329 | A1 | 5/2011 | Pusateri |
| 2011/0125539 | A1 | 5/2011 | Bollapragada et al. |
| 2012/0096385 | A1 | 4/2012 | Bank et al. |
| 2012/0116816 | A1 | 5/2012 | Smith |
| 2012/0226719 | A1 | 9/2012 | Sewall |
| 2013/0018674 | A1 | 1/2013 | Bedi et al. |
| 2013/0132105 | A1 | 5/2013 | Wood-Salomon et al. |
| 2013/0132142 | A1 | 5/2013 | Wood-Salomon et al. |
| 2013/0151284 | A1 | 6/2013 | Cohen-Solal et al. |
| 2013/0218592 | A1 | 8/2013 | Hashmat |
| 2015/0066529 | A1 | 3/2015 | Lattuca et al. |
| 2015/0149193 | A1 | 5/2015 | Jester et al. |
| 2015/0149206 | A1 | 5/2015 | Jester et al. |

OTHER PUBLICATIONS

United States Patent and Trademark Office, "Non-Final Office Action," issued in connection with U.S. Appl. No. 14/091,812, dated Oct. 23, 2015, 24 pages.

United States Patent and Trademark Office, "Advisory Action," issued in connection with U.S. Appl. No. 14/091,812 dated Jul. 6, 2016, 4 pages.

United States Patent and Trademark Office, "Advisory Action," issued in connection with U.S. Appl. No. 14/091,769 dated Jul. 29, 2016, 14 pages.

United States Patent and Trademark Office, "Notice of Allowance," issued in connection with U.S. Appl. No. 14/091,812 dated Sep. 12, 2016, 10 pages.

United States Patent and Trademark Office, "Non-Final Office Action," issued in connection with U.S. Appl. No. 14/091,769 dated Oct. 14, 2016, 21 pages.

Burke et al., "The State of the Art of Nurse Rostering," Journal of Scheduling, 2004, pp. 441-499, vol. 7, Kluwer Academic Publishers, the Netherlands, (59 pages).

Dang et al., "An ontological knowledge framework for adaptive medical workflow," Journal of Biomedical Informatics, 2008, pp. 829-836, vol. 41, Knowledge Management, Siemens Corporate Research, Princeton, NJ, (8 pages).

Mack et al., "New Aspects of Image Distribution and Workflow in Radiology," Journal of Digital Imaging, May 2000, pp. 17-21, vol. 13 No. 2, W.B. Saunders Company, Witten, Germany, (5 pages).

Meyer et al., "A Database Program for the Management of Staff Scheduling in a Radiology Department," Presented at the annual meeting of the Society for Pediatric Radiology, St. Louis, May 1997, American Journal of Roentgenology, pp. 1489-1492, vol. 169 (Dec. 1997), American Roentgen Ray Society, (4 pages).

Naidu et al., "Managing Personnel through Staff Scheduling Algorithms," Proceedings of the Fifth Joint Conference on Information Sciences, 2000, pp. 829-835, vol. 5 No. 2, Duke University, Durham, NC, (7 pages).

Welter et al., "Workflow management of content-based image retrieval for CAD support in PACS environments based on IHE," International Journal for Computer Assisted Radiology and Surgery, published Apr. 9, 2010, pp. 393-400, vol. 5, Aachen University Hospital, Aachen, Germany, (8 pages).

United States Patent and Trademark Office, "Final Office Action," issued in connection with U.S. Appl. No. 14/091,812 dated Apr. 27, 2016, 26 pages.

United States Patent and Trademark Office, "Final Office Action," issued in connection with U.S. Appl. No. 14/091,769 dated May 9, 2016, 28 pages.

United States Patent and Trademark Office, "Non-final Office Action," issued in connection with U.S. Appl. No. 14/091,769, dated May 19, 2017, 37 pages.

United States Patent and Trademark Office, "Advisory Action," issued in connection with U.S. Appl. No. 14/091,769, on Aug. 3, 2017, 16 pages. (Copy not provided as this is a USPTO document. Applicant will provide reference upon request from examiner).

* cited by examiner

1000

| | Patient | Exam | Assigned | Allocated | Queued | Radiologist |
|---|---|---|---|---|---|---|
| | Patient 1 | Exam 1 | ○ | ○ | ○ | |
| | Patient 2 | Exam 2 | ● | ○ | ○ | Radiologist 2 |
| | Patient 3 | Exam 3 | ○ | ○ | ○ | |
| | Patient 4 | Exam 4 | ○ | ● | ● | Radiologist 1 |
| | Patient 5 | Exam 5 | ○ | ○ | ○ | |

MEDICAL EXAMS 1002, 1004, 1006, 1008, 1010, 1012

SCORECARDS                                             Exam 4

| Staff Member | Experience | Specialty | Modality | Body Part | Total |
|---|---|---|---|---|---|
| Radiologist 1 | 2 | 4 | 2 | 2 | 10 |
| Radiologist 2 | 1 | 0 | 2 | 2 | 5 |
| Radiologist 3 | 1 | 0 | 2 | 0 | 3 |
| Radiologist 4 | 2 | 0 | 0 | 0 | 2 |
| Radiologist 5 | 0 | 0 | 0 | 0 | 0 |

SYSTEMS AND METHODS TO OPTIMIZE RADIOLOGY EXAM DISTRIBUTION

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored can include patient medication orders, medical histories, imaging data, test results, diagnosis information, management information, and/or scheduling information, for example.

BRIEF SUMMARY

Example methods, systems, and computer readable media are disclosed to allocate a medical exam. An example method includes identifying an exam characteristic associated with the medical exam. The example method includes determining a plurality of allocation scores for a plurality of radiologists by comparing the exam characteristic to a radiologist characteristic for each of the plurality of radiologists. The example method includes determining one of the plurality of allocation scores with a highest value. The example method includes allocating the medical exam to one of the plurality of radiologists associated with the one of the plurality of allocation scores with the highest value. The example method includes marking the medical exam as allocated to the one of the plurality of radiologists associated with the one of the plurality of allocation scores with the highest value. The example method includes providing an indication that the medical exam is allocated via a graphical user interface.

An example system includes an allocation manager to identify an exam characteristic associated with the medical exam. The example allocation manager is to determine a plurality of allocation scores for a plurality of radiologists by comparing the exam characteristic to a radiologist characteristic for each of the plurality of radiologists. The example allocation manager is to determine one of the plurality of allocation scores with a highest value. The example allocation manager is to allocate the medical exam to one of the plurality of radiologists associated with the one of the plurality of allocation scores with the highest value. The example allocation manager is to mark the medical exam as allocated to the one of the plurality of radiologists associated with the one of the plurality of allocation scores with the highest value. The example allocation manager is to provide an indication that the medical exam is allocated via a graphical user interface.

An example tangible computer readable storage medium comprises instructions that, when executed, cause a computing device to identify an exam characteristic associated with the medical exam. The example instructions cause the computing device to determine a plurality of allocation scores for a plurality of radiologists by comparing the exam characteristic to a radiologist characteristic for each of the plurality of radiologists. The example instructions cause the computing device to determine one of the plurality of allocation scores with a highest value. The example instructions cause the computing device to allocate the medical exam to one of the plurality of radiologists associated with the one of the plurality of allocation scores with the highest value. The example instructions cause the computing device to mark the medical exam as allocated to the one of the plurality of radiologists associated with the one of the plurality of allocation scores with the highest value. The example instructions cause the computing device to provide an indication that the medical exam is allocated via a graphical user interface.

BRIEF DESCRIPTION OF SEVERAL VIEWS OF THE DRAWINGS

FIG. 10 illustrates an example interface created by the example medical exam distributor of FIGS. 1 and/or 2.

FIG. 11 illustrates another example interface created by the example medical exam distributor of FIGS. 1 and/or 2.

Figure 1:
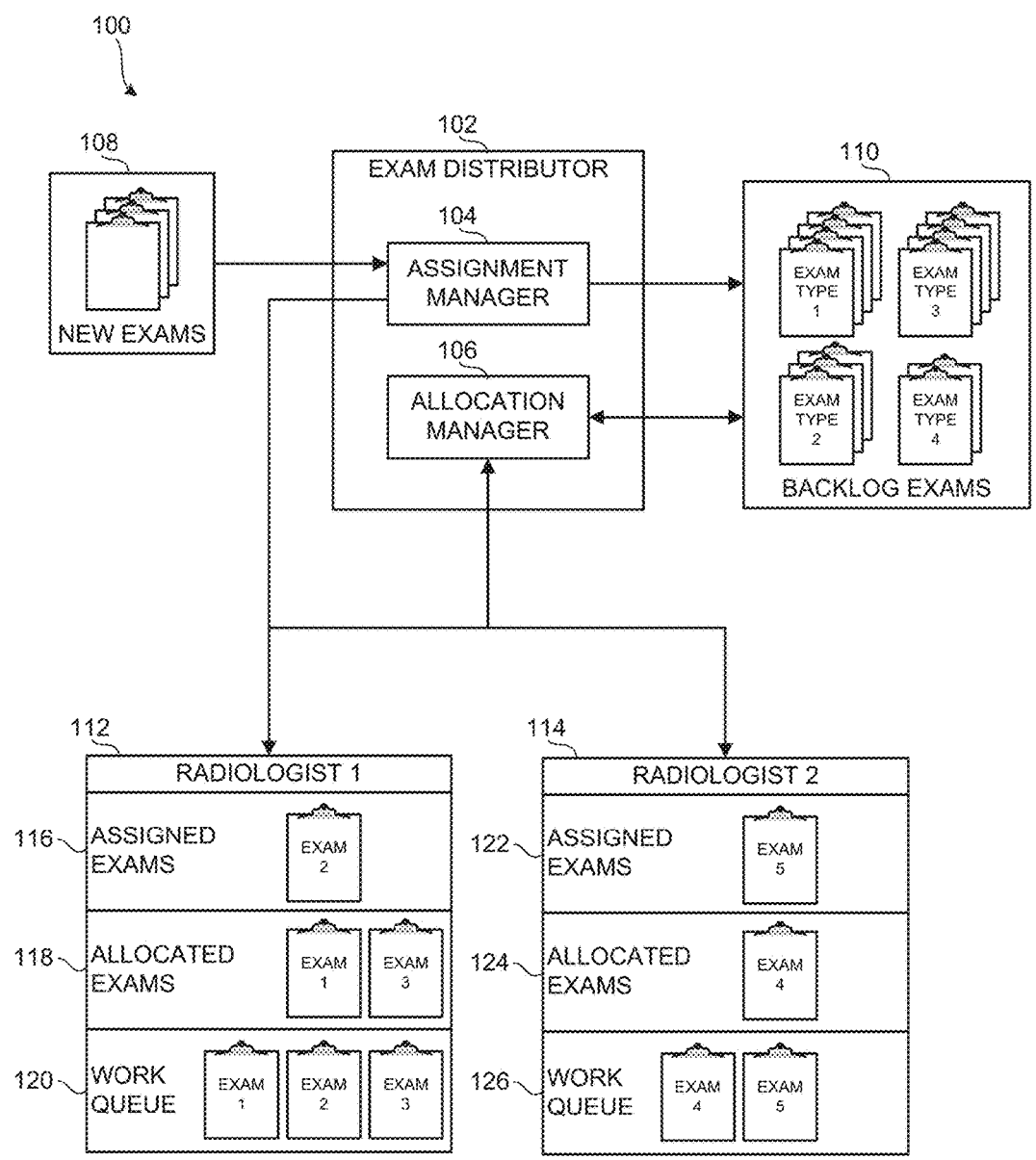
FIG. 1 illustrates a block diagram of an example medical exam distributor in an example healthcare system.

The foregoing summary, as well as the following detailed description of certain examples of the present invention, will be better understood when read in conjunction with the appended drawings. For the purpose of illustrating the invention, certain examples are shown in the drawings. It should be understood, however, that the present invention is not limited to the arrangements and instrumentality shown in the attached drawings.

DETAILED DESCRIPTION OF CERTAIN EXAMPLES

Although the following discloses example methods, systems, and tangible computer-readable media including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, and tangible computer-readable media, the examples provided are not the only way to implement such methods, systems, and tangible computer-readable media.

When any of the appended claims are read to cover a purely software and/or firmware implementation, in an embodiment, at least one of the elements is hereby expressly defined to include a tangible medium. As used herein, the term tangible computer readable medium is expressly defined to include any type of computer readable storage and to exclude propagating signals. Additionally or alternatively, the example methods, systems, and tangible computer-readable media can be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Many healthcare environments include radiology information systems to facilitate patient examination and/or patient diagnosis. For example, a radiology information system in a healthcare system stores radiology reports, messages, warning, alerts, patient scheduling information, patient demographic data, patient tracking information, and/or physician and patient status monitors. A radiology information system can also enable exam order entering (e.g., ordering an x-ray of a patient) and image and film tracking (e.g., tracking identities of one or more people that have checked a film).

A medical exam may be ordered for a patient, and the medical exam is assigned to a practitioner (e.g., a radiologist) to conduct the exam. A practitioner may have a workflow comprising one or more medical exams to be conducted and an order in which the one or more medical exams are to be conducted. Examples described herein provide a medical exam distributor to distribute medical exams on behalf of, for example, a radiology information system. Example exam distributors described herein enable efficient assignment and/or allocation of medical exams to practitioners (e.g., radiologists) and management of practitioner workflows.

In some examples, profiles are created for radiologists to be used by the example exam distributors to assign and/or allocate medical exams. A radiologist profile can identify a radiologist, an experience level of the radiologist (e.g., a resident, an attending, etc.), a specialty associated with the radiologist (e.g., emergency, pediatrics, etc.), a modality preferred by the radiologist (e.g., a computed tomography (CT) scan, a magnetic resonance imaging (MRI) exam, etc.), and/or a body part preferred by the radiologist (e.g., abdomen, chest, etc.). A radiologist profile can also identify days and/or times during which the radiologist practices with the preferred specialty, modality, and/or body part. For example, a radiologist may work in an emergency department on Mondays and Tuesdays, and may work in a pediatrics department on Wednesdays, Thursdays, and Fridays. A radiologist profile can also identify locations at which the radiologist practices the preferred specialty, modality, and/or body part. For example, a radiologist may work at Hospital A on Mondays and Tuesdays, and may work at Hospital B on Wednesdays, Thursdays, and Fridays. In some examples, multiple profiles are created for a radiologist. For example, if a radiologist works at different locations, and/or works on different specialties, modalities, and/or body parts at different days and/or times, a profile can be created for the radiologist for each location, each day, and/or each time. The radiologist profiles are used by the example medical exam distributor to assign and/or allocate medical exams and/or manage radiologist workflows.

In some examples, distribution rules are defined to enable the assignment and/or allocation of medical exams. Distribution rules include queue length rules, matching rules, priority rules, and/or more generally, load-balancing rules that define the allocation and assignment of exams in view of exam and radiologist attributes. In some examples, a queue length rule defines a length of a radiologist workflow. For example, a queue length rule defines that a radiologist workflow comprises a queue length of five (e.g., a maximum of five exams can be assigned and/or allocated to a radiologist at one time).

In some examples, matching rules define how radiologists are to be matched with a medical exam to be distributed. A medical exam to be distributed can be associated with a specialty, a modality, and/or a body part. In some examples, a matching rule defines that a radiologist is to be matched with a medical exam when a specialty associated with the radiologist matches a specialty associated with the medical exam, when a modality associated with the radiologist matches a modality associated with the medical exam, and/or when a body part associated with the radiologist matches a body part associated with the medical exam. Matching rules also define point values associated with a specialty match, a modality match, and/or a body part match. Point values are used to weight the matching process so that, for example, a match in a specialty is given more weight than a match in a body part. For example, a match between a specialty associated with a radiologist and a specialty associated with a medical exam may afford the radiologist ten (10) points. A match between a modality associated with a radiologist and a modality associated with a medical exam may afford the radiologist five (5) points. A match between a body part associated with a radiologist and a body part associated with a medical exam may afford the radiologist two (2) points.

In some examples, a priority and/or flag rule defines that a medical exam marked with a priority flag is to be moved to a top position or queue of a radiologist workflow such that the radiologist will conduct the medical exam before conducting other medical exams. For example, a radiologist may determine that a medical exam is urgent and mark the exam with a priority flag. The medical exam is then moved to the top of the radiologist workflow.

In some examples, load-balancing rules are used to increase the efficiency of the exam assignment and/or allocation process and/or the exam review process. In some examples, a load-balancing rule is used to increase a likelihood that a service level agreement associated with a patient and/or a healthcare provider is met. For example, a service level agreement (SLA) can include a length of time during which a medical exam is to be conducted. In such an example, a load-balancing rule defines that if the length of time during which a medical exam is to be conducted is approaching (e.g., within a threshold amount of time), the medical exam is to be escalated and moved to the top of a radiologist workflow (e.g., a first position of the workflow queue). For example, if a medical exam is to be conducted within one hour to maintain the time constraints of a service level agreement, the medical exam will be moved to a top position or queue of a radiologist workflow such that the radiologist will conduct the medical exam before conducting other medical exams.

In some examples, a load-balancing rule is used to increase a likelihood that a radiologist with sufficient experience is assigned to a medical exam associated with a relative value unit score. A relative value unit (RVU) score is a measure of value for practitioner services. A relative value unit score can be associated with a level of experience of a radiologist. For example, a medical exam with a high relative value unit score may be a more difficult exam to conduct and, thus, a more experienced radiologist is to conduct the exam. In some examples, a load-balancing rule defines that a medical exam is to be removed from a radiologist workflow if the radiologist does not have sufficient experience to conduct the medical exam based on a relative value unit score of the medical exam.

In some examples, a medical exam is assigned to a radiologist based on the load-balancing rules. For example, when a medical exam is to be examined, a practitioner (e.g., an attending) and/or an administrator can assign the medical exam to another radiologist (e.g., a resident). Examples disclosed herein determine if the assigned radiologist is available to examine the medical exam using, for example, the profile of the assigned radiologist. For example, if the profile of the assigned radiologist specifies that the radiologist is at Hospital A, and the medical exam to be assigned is at Hospital B, the radiologist is not available to be assigned to the medical exam. If the radiologist is available, examples disclosed herein assign the medical exam to the radiologist.

If the radiologist is not available, the assigning practitioner can specify whether to wait till the desired radiologist is available to assign the medical exam to the desired radiologist. If the assigning practitioner wishes to wait till the desired radiologist is available, a waiting flag is set, and the availability of the desired radiologist is monitored. Once available, the desired radiologist is assigned to the medical exam. If the assigning practitioner does not wish to wait till the desired radiologist is available, examples disclosed herein allocate the medical exam to another radiologist (e.g., the system automatically selects a radiologist and moves the medical exam to the selected radiologist's workflow).

In some examples, the radiologist accepts the assignment. If the radiologist accepts the assignment of the medical exam, an assignment flag is set, and the medical exam is moved to the radiologist's workflow. In some examples, the radiologist declines the assignment. For example, a radiologist may have a full workflow and, thus, may not want to add the medical exam being assigned (e.g., which may require removing another medical exam in the radiologist's workflow). If the radiologist declines the assignment, the medical exam may be assigned to another radiologist. If the medical exam is not assigned to another radiologist (e.g., if a practitioner does not select another radiologist to take the exam), examples disclosed herein allocate the medical exam to a radiologist (e.g., the system automatically selects a radiologist and moves the medical exam to the selected radiologist's workflow).

In some examples, a medical exam is allocated to a radiologist. For example, a medical exam is allocated to a radiologist when the medical exam has not been assigned by a practitioner to a radiologist, and has not yet been automatically assigned to a radiologist. To allocate a medical exam, examples described herein identify exam characteristics of the medical exam. Exam characteristics include, for example, location, experience level, specialty, modality, and/or body part associated with the medical exam to be allocated. Examples disclosed herein identify available radiologists and use the matching rules and point values to determine a radiologist that best matches the medical exam to be allocated.

To determine a best match for the medical exam to be allocated, examples described herein determine an allocation score for each available radiologist for the medical exam. To determine an allocation score, examples disclosed herein assign point values for each characteristic associated with a radiologist that matches a characteristic of the medical exam. For example, if the medical exam is at a location that is the same as the radiologist, the radiologist is assigned and/or allocated a location point value (e.g., which has been previously specified during the defining of the matching rules). If an experience level associated with the medical exam (e.g., an experience level needed by a practitioner to conduct the medical exam) is the same as an experience level of the radiologist, the radiologist is assigned and/or allocated an experience point value. If a specialty associated with the medical exam is the same as a specialty associated with the radiologist, the radiologist is assigned and/or allocated a specialty point value. If a modality associated with the medical exam is the same as a modality associated with the radiologist, the radiologist is assigned and/or allocated a modality point value. If a body part associated with the medical exam is the same as a body part associated with the radiologist, the radiologist is assigned and/or allocated a body part point value. Examples disclosed herein total the point values assigned and/or allocated to the radiologist to determine the overall allocation score. Allocation scores are determined for each available radiologist so that the allocation scores can be compared.

To compare allocations scores for available radiologists, examples described herein prepare scorecards for each of the available radiologists using the allocation scores. Example scorecards identify the radiologist, the overall allocation score of the radiologist, and each of the point values allocated to the radiologist that make up the overall allocation score. The scorecards can be viewed by a practitioner to see how well a radiologist matches a medical exam to be allocated.

Examples disclosed herein determine the available radiologist with the highest allocation score. If a particular radiologist has the highest allocation score (e.g., a single allocation score is the highest allocation score), the medical exam is allocated to the radiologist with the highest allocation score. If more than one radiologist has the highest allocation score (e.g., if there is a tie between allocation scores), examples described herein determine the radiologist with the highest allocation score and the shortest workflow queue length. For example, a first and a second radiologist may both obtain an allocation score of twelve, but the first radiologist may have a queue length of three while the second radiologist has a queue length of four. Examples described herein allocate the medical exam to the radiologist with the highest allocation score and the shortest workflow queue length (e.g., the first radiologist) so that the medical exam will be examined more quickly than if the medical exam was allocated to a radiologist with a longer queue length.

In some examples, a radiologist accepts or declines the allocation of the medical exam. If the radiologist accepts the allocation of the medical exam, an allocation flag is set and the medical exam is moved to the radiologist's workflow. If the radiologist declines the allocation of the medical exam, an allocation rejection entry is recorded for the radiologist. Examples described herein maintain logs of rejections of exam allocations by radiologists so that a practitioner can review such rejections. For example, if a radiologist is declining numerous exam allocations and/or a particular type of exam allocation, a practitioner (e.g., an attending) may wish to review this information (e.g., so that the practitioner may intervene).

In some examples, load-balancing rules are applied once a medical exam has been assigned and/or allocated to a radiologist. Load-balancing rules are used to increase the efficiency of the exam assignment and/or allocation process and/or the exam review process. In some examples, it is determined if a priority flag has been set for a medical exam. If a priority flag has been set, the medical exam is moved to the top of the radiologist's workflow (e.g., so that the medical exam will be conducted prior to other medical exams in the workflow). If there is a service level agreement associated with the medical exam, examples described herein determine if there is sufficient time to perform the medical exam before the expiry of the time period defined in the service level agreement. If there is not sufficient time to perform the medical exam, the medical exam is moved to the top of the radiologist's workflow. If there is a relative value unit score associated with the medical exam, examples described herein determine if the experience level of the radiologist is sufficient for the relative value unit score of the medical exam. For example, a medical exam with a particular relative value unit score may require the exam to be performed by a practitioner with a particular level of experience. If the experience level of the assigned and/or allocation radiologist is not sufficient for the relative value unit score of the medical exam, an assignment and/or allocation flag for the radiologist is removed so that the medical exam is removed from the radiologist's workflow. The medical exam can then be assigned and/or allocated to another radiologist.

In some examples, a radiologist assigns an available medical exam to himself. For example, a radiologist can view all unassigned and/or unallocated medical exams and select a particular medical exam he wishes to perform. Examples described herein assign the exam to the radiologist, set an assignment flag, and move the selected medical exam to the radiologist's workflow. Examples described herein determine if the queue length of the radiologist's workflow exceeds a threshold queue length (e.g., it is determined if the newly selected medical exam causes the workflow to be too long). If the queue length of the radiologist's workflow exceeds the threshold queue length, examples described herein determine the medical exam in the workflow that has the lowest allocation score (e.g., using the allocation scorecards). The assignment and/or allocation flag is removed for the medical exam with the lowest allocation score, and the medical exam is removed from the radiologist's workflow.

In other examples, after applying one or more of the load-balancing rules, the exam distributor 102 automatically delivers an exam to a radiologist who is online and accessing the system in real-time rather than delivering the exam to the radiologist's work queue. For example, a radiologist can select to receive exams to review in real-time such that the exam distributor assigns the radiologist an exam based on the load-balancing rules; the exam is presented for review via, for example, a reading tool accessible via the user interface; and the radiologist reviews the exam immediately or substantially immediately upon receiving the exam via the reading tool, without the exam being queued in the radiologist workflow for review at a later time. Thus, the exam distributor 102 provides for flexibility in exam review by delivering an exam to the radiologist's work queue for later review or by providing substantially immediate access to the assigned exam by auto-serving the exams to the radiologist.

FIG. 1 shows a block diagram of an example healthcare system 100 capable of implementing an example medical exam distributor 102. The example medical exam distributor 102 enables efficient assignment and/or allocation of medical exams to radiologists and management of radiologist workflows.

The example exam distributor 102 includes an example assignment manager 104 and an example allocation manager 106. The example assignment manager 104 controls assignments of medical exams to radiologists. Exams are assigned to radiologists when radiologists select themselves or other radiologists to conduct the medical exams. The example allocation manager 106 controls allocations of medical exams to radiologists. Exams are allocated to radiologists when the exams have not been assigned by a radiologist, and are to be automatically allotted to a radiologist.

When a medical exam is assigned and/or allocated to a radiologist, the example medical exam distributor 102 adds the medical exam to a workflow associated with the radiologist. A radiologist workflow includes a listing of medical exams to be conducted by a radiologist, and an order in which the exams are to be conducted. The radiologist workflow indicates what medical exams have been assigned to the radiologist and what medical exams have been allocated to the radiologist.

In operation, new medical exams 108 are ordered to be conducted for a plurality of patients. The example assignment manager 104 determines if any of the new medical exams 108 are to be assigned to particular radiologists. New medical exams 108 will be assigned to particular radiologists when a user makes a selection of a medical exam and a selection of a particular radiologist. If one of the new medical exams 108 is to be assigned to a particular radiologist, the example assignment manager adds the medical exam to the radiologist's workflow.

Medical exams that are not assigned to radiologists are backlog exams 110. The example backlog exams 110 are stored by exam type and/or characteristic (e.g., by location, specialty, sub-specialty, modality, body part, etc.). The example allocation manager 106 automatically allocates the backlog exams 110 to radiologists based on the exam type and/or characteristic(s). The example allocation manager 106 uses the exam characteristic(s) to determine radiologists that best match the exams. When one of the backlog exams 110 is allocated to a radiologist by the example allocation manager 106, the exam is added to the radiologist's workflow.

The illustrated example includes a first radiologist workflow 112 and a second radiologist workflow 114. The example first radiologist workflow 112 includes first assigned exams 116, first allocated exams 118, and a first work queue 120. The first assigned exams 116 show exams assigned by the example assignment manager 104 to Radiologist 1 (e.g., Exam 2). The first allocated exams 118 show exams allocated by the example allocation manager 106 to Radiologist 1 (e.g., Exam 1 and Exam 3). The first work queue 120 shows the listing of exams to be conducted by Radiologist 1 (e.g., Exam 1, then Exam 2, then Exam 3).

The example second radiologist workflow 114 includes second assigned exams 122, second allocated exams 124, and a second work queue 126. The second assigned exams 122 show exams assigned by the example assignment manager 104 to Radiologist 2 (e.g., Exam 5). The second allocated exams 124 show exams allocated by the example allocation manager 106 to Radiologist 2 (e.g., Exam 4). The second work queue 126 shows the listing of exams to be conducted by Radiologist 2 (e.g., Exam 4, then Exam 5).

Figure 2:
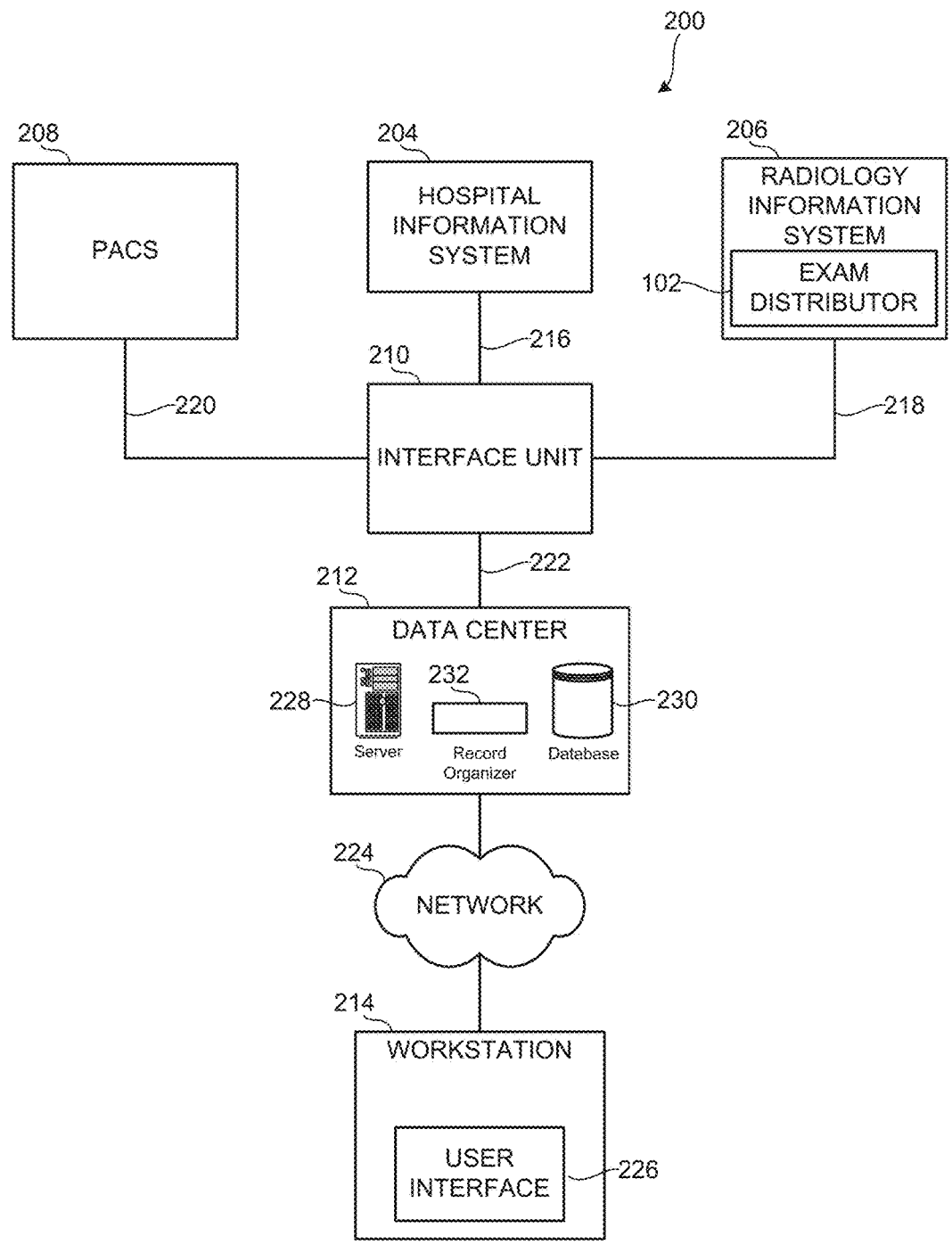
FIG. 2 illustrates another block diagram of the example medical exam distributor in an example healthcare system.

FIG. 2 shows a block diagram of an example healthcare system 200 capable of implementing the example medical exam distributor 102 of FIG. 1. The example healthcare system 200 includes the example medical exam distributor 102, a hospital information system (HIS) 204, a radiology information system (RIS) 206, a picture archiving and communication system (PACS) 208, an interface unit 210, a data center 212, and a workstation 214. In the illustrated example, the HIS 204, the RIS 206, and the PACS 208 are housed in a healthcare facility and locally archived. However, in other implementations, the HIS 204, the RIS 206, and/or the PACS 208 can be housed one or more other suitable locations. In certain implementations, one or more of the PACS 208, RIS 206, HIS 204, etc., can be implemented remotely via a thin client and/or downloadable software solution. Furthermore, one or more components of the healthcare system 200 can be combined and/or implemented together. For example, the RIS 206 and/or the PACS 208 can be integrated with the HIS 204; the PACS 208 can be integrated with the RIS 206; and/or the three example information systems 204, 206, and/or 208 can be integrated together. In other example implementations, the healthcare system 200 includes a subset of the illustrated information systems 204, 206, and/or 208. For example, the healthcare system 200 can include only one or two of the HIS 204, the RIS 206, and/or the PACS 208. Information (e.g., scheduling, test results, observations, diagnosis, etc.) can be entered into the HIS 204, the RIS 206, and/or the PACS 208 by healthcare practitioners (e.g., radiologists, physicians, and/or technicians) before and/or after patient examination. In some examples, the medical exam distributor 202 is located in the RIS 206. In some examples, the example medical exam distributor 202 is located separately or is included in any other suitable device of the healthcare system 200.

The HIS 204 stores medical information such as clinical reports, patient information, and/or administrative information received from, for example, personnel at a hospital, clinic, and/or a physician's office. The RIS 206 stores information such as, for example, radiology reports, messages, warnings, alerts, patient scheduling information, patient demographic data, patient tracking information, and/or physician and patient status monitors. Additionally, the RIS 206 enables exam order entry (e.g., ordering an x-ray of a patient) and image and film tracking (e.g., tracking identities of one or more people that have checked out a film). In some examples, information in the RIS 206 is formatted according to the HL-7 (Health Level Seven) clinical communication protocol.

The PACS 208 stores medical images (e.g., x-rays, scans, three-dimensional renderings, etc.) as, for example, digital images in a database or registry. In some examples, the medical images are stored in the PACS 208 using the Digital Imaging and Communications in Medicine ("DICOM") format. Images are stored in the PACS 208 by healthcare practitioners (e.g., imaging technicians, physicians, radiologists) after a medical imaging of a patient and/or are automatically transmitted from medical imaging devices to the PACS 208 for storage. In some examples, the PACS 208 can also include a display device and/or viewing workstation to enable a healthcare practitioner or provider to communicate with the PACS 208.

The interface unit 210 includes a hospital information system interface connection 216, a radiology information system interface connection 218, a PACS interface connection 220, and a data center interface connection 222. The interface unit 210 facilities communication among the HIS 204, the RIS 206, the PACS 208, and/or the data center 212. The interface connections 216, 218, 220, and 222 can be implemented by, for example, a Wide Area Network ("WAN") such as a private network or the Internet. Accordingly, the interface unit 210 includes one or more communication components such as, for example, an Ethernet device, an asynchronous transfer mode ("ATM") device, an 802.11 device, a DSL modem, a cable modem, a cellular modem, etc. In turn, the data center 212 communicates with the workstation 214, via a network 224, implemented at a plurality of locations (e.g., a hospital, clinic, doctor's office, other medical office, or terminal, etc.). The network 224 is implemented by, for example, the Internet, an intranet, a private network, a wired or wireless Local Area Network, and/or a wired or wireless Wide Area Network. In some examples, the interface unit 210 also includes a broker (e.g., a Mitra Imaging's PACS Broker) to allow medical information and medical images to be transmitted together and stored together.

The interface unit 210 receives images, medical reports, administrative information, and/or other clinical information from the information systems 204, 206, 208 via the interface connections 216, 218, 220. If necessary (e.g., when different formats of the received information are incompatible), the interface unit 210 translates or reformats (e.g., into Structured Query Language ("SQL") or standard text) the medical information, such as medical reports, to be properly stored at the data center 212. The reformatted medical information can be transmitted using a transmission protocol to enable different medical information to share common identification elements, such as a patient name or social security number. Next, the interface unit 210 transmits the medical information to the data center 212 via the data center interface connection 222. Finally, medical information is stored in the data center 212 in, for example, the DICOM format, which enables medical images and corresponding medical information to be transmitted and stored together.

The medical information is later viewable and easily retrievable at the workstation 114 (e.g., by their common identification element, such as a patient name or record number). The workstation 214 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstation 214 receives commands and/or other input from a user via, for example, a keyboard, mouse, track ball, microphone, etc. The workstation 214 is capable of implementing a user interface 226 to enable a healthcare practitioner to interact with the healthcare system 200. For example, in response to a request from a physician, the user interface 226 presents a patient medical history.

The example data center 212 of FIG. 1 is an archive to store information such as, for example, images, data, medical reports, and/or, more generally, patient medical records. In addition, the data center 212 can also serve as a central conduit to information located at other sources such as, for example, local archives, hospital information systems/radiology information systems (e.g., the HIS 204 and/or the RIS 206), or medical imaging/storage systems (e.g., the PACS 208 and/or connected imaging modalities). That is, the data center 212 can store links or indicators (e.g., identification numbers, patient names, or record numbers) to information. In the illustrated example, the data center 212 is managed by an application server provider ("ASP") and is located in a centralized location that can be accessed by a plurality of systems and facilities (e.g., hospitals, clinics, doctor's offices, other medical offices, and/or terminals). In some examples, the data center 212 can be spatially distant from the HIS 204, the RIS 206, and/or the PACS 208 (e.g., at General Electric® headquarters).

The example data center 212 of FIG. 2 includes a server 228, a database 230, and a record organizer 232. The server 228 receives, processes, and conveys information to and from the components of the healthcare system 200. The database 230 stores the medical information described herein and provides access thereto. The example record organizer 232 of FIG. 2 manages patient medical histories, for example. The record organizer 232 can also assist in procedure scheduling, for example.

In many examples, a medical exam are ordered for a patient (e.g., via the user interface 226 at the workstation 214), and the medical exam is assigned to a practitioner (e.g., a radiologist) to conduct the exam. A radiologist may have a workflow comprising one or more medical exams to be conducted and an order in which the one or more medical exams are to be conducted. The example medical exam distributor 102 enables efficient assignment and/or allocation of medical exams to radiologists and management of radiologist workflows.

To enable efficient assignment and/or allocation of medical exams, the example medical exam distributor 102 creates one or more profiles for each radiologist capable of being assigned to a medical exam to be conducted. A radiologist profile identifies a radiologist, an experience level of the radiologist (e.g., a resident, an attending, etc.), a specialty associated with the radiologist (e.g., emergency, pediatrics, etc.), a modality preferred by the radiologist (e.g., a computed tomography (CT) scan, a magnetic resonance imaging (MRI) exam, etc.), and/or a body part preferred by the radiologist (e.g., abdomen, chest, etc.). A radiologist profile also identifies days and/or times during which the radiologist practices with the preferred specialty, modality, and/or body part. A radiologist profile also identifies locations at which the radiologist practices the preferred specialty, modality, and/or body part. In some examples, multiple profiles are created for a radiologist. For example, if a radiologist works at different locations, and/or works on different specialties, modalities, and/or body parts at different days and/or times, a profile is created for the radiologist for each location, each day, and/or each time.

The radiologist profiles are used by the example medical exam distributor 102 to assign and/or allocate medical exams and/or manage radiologist workflows. As used herein, an assignment of a medical exam refers to a selection of a practitioner to conduct a medical exam. For example, a radiologist can select to assign a medical exam to himself or to assign a medical exam to another radiologist. A selection to assign a radiologist to a medical exam can be made, for example, via the user interface 226. If an assignment of a medical exam is made, the example medical exam distributor 102 moves the medical exam to a workflow of the assigned radiologist.

As used herein, an allocation of a medical exam refers to an automatic assignment of a medical exam to a practitioner by the example medical exam distributor 102 without user input. For example, if a medical exam has not been assigned to a radiologist (e.g., by a user), the example medical exam distributor 102 determines a radiologist to whom the medical exam is to be allocated. To allocate a medical exam, the example medical exam distributor 102 identifies exam characteristics of the medical exam. Exam characteristics include, for example, location, experience level, specialty, modality, and/or body part associated with the medical exam to be allocated. The example medical exam distributor 102 uses the exam characteristics and the radiologist profiles to determine a radiologist that best matches the medical exam to be allocated.

To determine a best match for the medical exam to be allocated, the example medical exam distributor 102 determines an allocation score for each available radiologist for the medical exam. To determine an allocation score, the example medical exam distributor 102 assigns point values for each characteristic associated with a radiologist that matches a characteristic of the medical exam. For example, if the medical exam is at a location that is the same as the radiologist, the radiologist is assigned and/or allocated a location point value. If an experience level associated with the medical exam (e.g., an experience level needed by a practitioner to conduct the medical exam) is the same as an experience level of the radiologist, the radiologist is assigned and/or allocated an experience point value. If a specialty associated with the medical exam is the same as a specialty associated with the radiologist, the radiologist is assigned and/or allocated a specialty point value. If a modality associated with the medical exam is the same as a modality associated with the radiologist, the radiologist is assigned and/or allocated a modality point value. If a body part associated with the medical exam is the same as a body part associated with the radiologist, the radiologist is assigned and/or allocated a body part point value. The example medical exam distributor 102 totals the point values assigned and/or allocated to the radiologist to determine the overall allocation score. The example medical exam distributor 102 determines allocation scores for each available radiologist so that the allocation scores can be compared.

The example medical exam distributor 102 determines the available radiologist with the highest overall allocation score and allocates the medical exam to the radiologist with the highest overall allocation score. The example medical exam distributor 102 facilitates user assignment of medical exams and/or automatic allocation of medical exams. The example medical exam distributor 102 enables efficient management of practitioner workflows.

Flowcharts representative of example machine readable instructions for implementing the example campaign manager 102 of FIG. 1 are shown in FIGS. 3, 4, 5, 6, 7, 8, and/or 9. In these examples, the machine readable instructions comprise programs for execution by a processor such as the processor 1312 shown in the example processor platform 1300 discussed below in connection with FIG. 13. The programs can be embodied in software stored on a tangible computer readable storage medium such as a CD-ROM, a floppy disk, a hard drive, a digital versatile disk (DVD), a Blu-ray disk, or a memory associated with the processor 1312, but the entire programs and/or parts thereof could alternatively be executed by a device other than the processor 1312 and/or embodied in firmware or dedicated hardware. Further, although the example programs are described with reference to the flowcharts illustrated in FIGS. 3, 4, 5, 6, 7, 8, and/or 9, many other methods of implementing the example campaign manager 102 can alternatively be used. For example, the order of execution of the blocks can be changed, and/or some of the blocks described can be changed, eliminated, or combined.

As mentioned above, the example processes of FIGS. 3, 4, 5, 6, 7, 8, and/or 9 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and transmission media. As used herein, "tangible computer readable storage medium" and "tangible machine readable storage medium" are used interchangeably. Additionally or alternatively, the example processes of FIGS. 3, 4, 5, 6, 7, 8, and/or 9 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and transmission media. As used herein, when the phrase "at least" is used as the transition term in a preamble of a claim, it is open-ended in the same manner as the term "comprising" is open ended.

Figure 3:
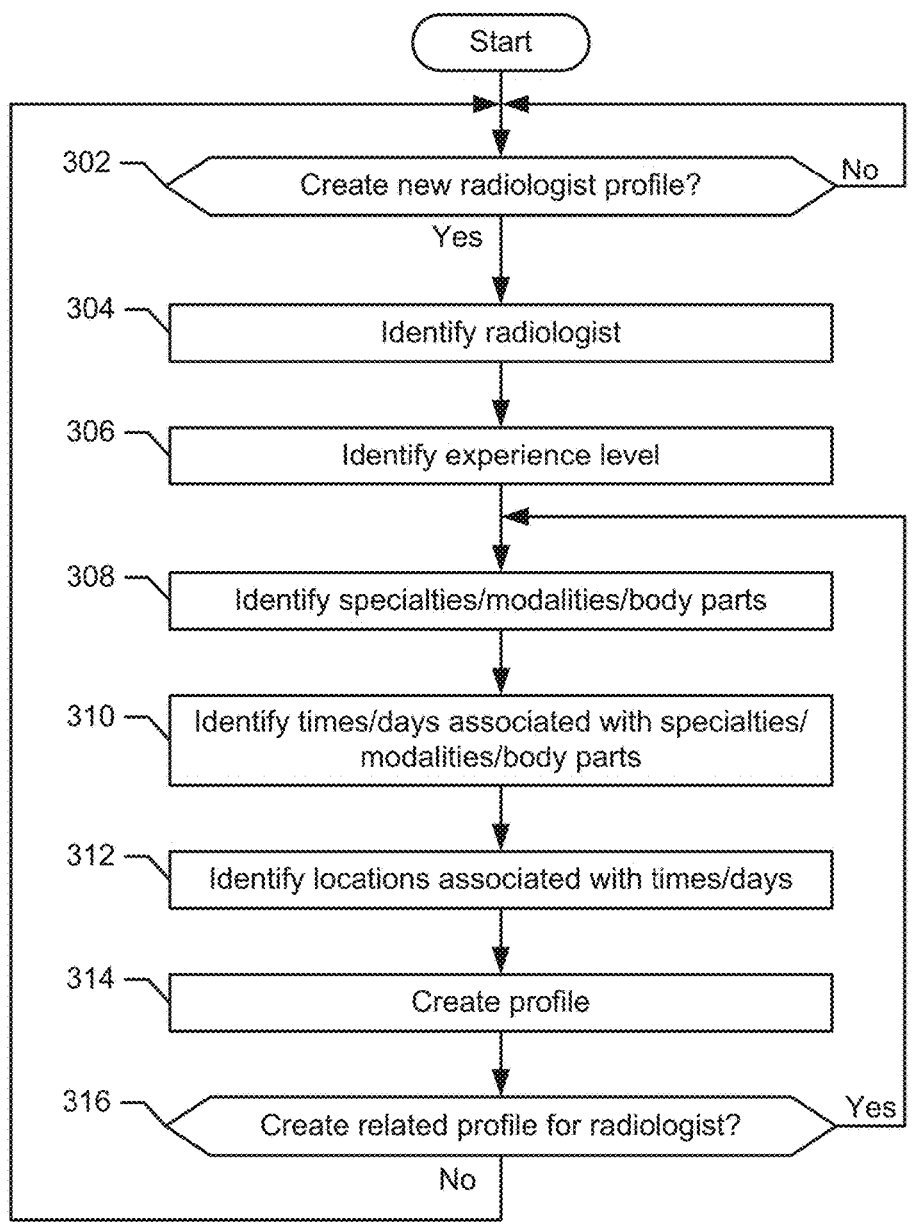
FIG. 3 is a flow diagram illustrating an example method for creating radiologist profiles at the example medical exam distributor of FIGS. 1 and/or 2.

FIG. 3 is a flow diagram illustrating an example method for creating radiologist profiles and/or other identifying information for particular radiologists at the example medical exam distributor 102 of FIGS. 1 and/or 2. Profiles are created for radiologists to be used by the example exam distributor 102 to assign and/or allocate medical exams. Initially, the example medical exam distributor 102 determines if a new radiologist profile is to be created (block 302). A new radiologist profile can be created, for example, when the example medical exam distributor 102 is initially implemented, when a new radiologist is employed, when a radiologist has a new schedule, etc. A radiologist can create a new profile using the example medical exam distributor 102 via, for example, the user interface 226 of FIG. 2. Control remains at block 302 until a new radiologist profile is to be created.

When a new radiologist profile is to be created, a radiologist for the profile is identified (block 304). An experience level of the radiologist is then identified (block 306). An experience level may be, for example, a number of years the radiologist has been practicing and/or a title indicative of the experience level such as a resident, an intern, an attending, etc. A specialty, modality and/or body part preferred by the radiologist are identified (block 308). A specialty preferred by the radiologist may be, for example, pediatrics, emergency, etc. A modality preferred by the radiologist may be, for example, a computed tomography (CT) scan, a magnetic resonance imaging (MRI) exam, etc. A body part preferred by a radiologist may be, for example, an abdomen, a chest, etc. Identifying a specialty, modality and/or body part preferred by the radiologist allows the example medical exam distributor 102 to assign and/or allocate exams to the radiologist that the radiologist may possess increased skills in performing.

Days and/or times during which the radiologist practices with the preferred specialty, modality, and/or body part are also identified (block 310). For example, a radiologist may work in an emergency department on Mondays and Tuesdays, and may work in a pediatrics department on Wednesdays, Thursdays, and Fridays. Locations at which the radiologist practices the preferred specialty, modality, and/or body part are also identified (block 312). For example, a radiologist may work at Hospital A on Mondays and Tuesdays, and may work at Hospital B on Wednesdays, Thursdays, and Fridays. Identifying times, days, and/or locations during which the radiologist is associated with particular medical areas enables the example medical exam distributor 102 to efficiently assign and/or allocate medical exams.

The example medical exam distributor 102 creates a profile for the radiologist using the identified information (block 314). The example medical exam distributor 102 stores the profile and creates a visual representation of the profile for viewing at, for example, the user interface 226.

The example medical exam distributor 102 determines if a related profile is to be created for the radiologist (block 316). In some examples, multiple profiles are created for a radiologist. For example, if a radiologist works at different locations, and/or works on different specialties, modalities, and/or body parts at different days and/or times, a profile can be created for the radiologist for each location, each day, and/or each time. If a related profile is to be created, control returns to block 308 where a specialty, modality, and/or body part, and a time, day, and/or location are identified to be associated with the radiologist in a new profile. If a related profile is not to be created, control returns to block 302.

Figure 4:
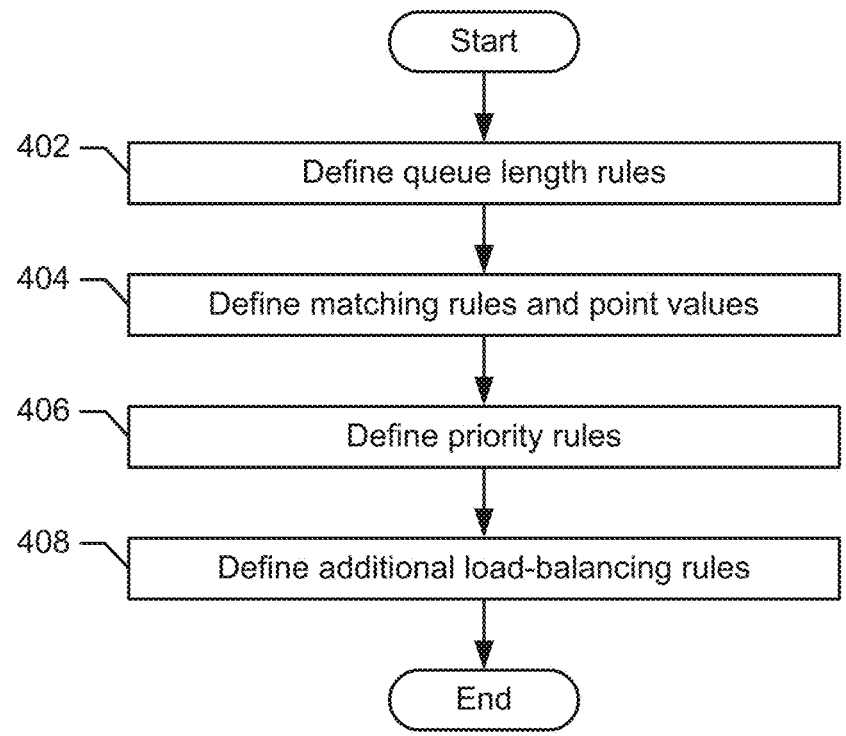
FIG. 4 is a flow diagram illustrating an example method for initiating use of the example medical exam distributor of FIGS. 1 and/or 2.

FIG. 4 is a flow diagram illustrating an example method for initiating use of the example medical exam distributor 102 of FIGS. 1 and/or 2. The example medical exam distributor 102 enables a user to define distribution rules to be used in assigning and/or allocating medical exams. Distribution rules include queue length rules, matching rules, priority rules, and/or more generally, load-balancing rules defining parameters for exam distribution based on exam and radiologist attributes. Initially, a queue length rule is defined to specify a length of a radiologist workflow (block 402). For example, a queue length rule defines that a radiologist workflow comprises a queue length of five (e.g., a maximum of five exams may be assigned and/or allocated to a radiologist at one time).

Matching rules and point values are then defined (block 404). In some examples, matching rules define how radiologists are to be matched with a medical exam to be distributed by the example medical exam distributor 102. A medical exam to be distributed can be associated with a specialty, a modality, and/or a body part, for example. In some examples, a matching rule defines that a radiologist is to be matched with a medical exam when a specialty associated with the radiologist matches a specialty associated with the medical exam, when a modality associated with the radiologist matches a modality associated with the medical exam, and/or when a body part associated with the radiologist matches a body part associated with the medical exam, for example. Instead of or in addition to a radiologist specialty, a radiologist's experience with a certain type of exam (e.g., number of exams of the type read, number of hours spent reviewing the type of exam, etc.) can be a factor in matching, for example. Matching rules also define point values associated with a specialty match, a modality match, and/or a body part match. Point values are used to weight the matching process so that, for example, a match in a specialty is given more weight than a match in a body part. For example, a match between a specialty associated with a radiologist and a specialty associated with a medical exam may afford the radiologist ten (10) points. A match between a modality associated with a radiologist and a modality associated with a medical exam may afford the radiologist five (5) points. A match between a body part associated with a radiologist and a body part associated with a medical exam may afford the radiologist two (2) points.

Priority rules are then defined (block 406). In some examples, a priority rule defines that a medical exam marked with a priority flag is to be moved to a top position or queue of a radiologist workflow by the example medical exam distributor 102 such that the radiologist will conduct the medical exam before conducting other medical exams. For example, a radiologist can determine that a medical exam is urgent and mark the exam with a priority flag. The example medical exam distributor 102 the moves the medical exam to the top of the radiologist workflow. The example method of FIG. 4 then ends.

In some examples, additional load-balancing rules are defined for distributing exams (block 408). Such additional load-balancing rules can be customized based on needs and/or goals of the healthcare institution. For example, load-balancing rules are used by the example medical exam distributor 102 to increase the efficiency of the exam assignment and/or allocation process and/or the exam review process. In some examples, a load-balancing rule is used to increase a likelihood that a service level agreement associated with a patient and/or a healthcare provider is met. For example, a service level agreement can include a length of time during which a medical exam is to be conducted. In such an example, a load-balancing rule defines that if the length of time during which a medical exam is to be conducted is approaching (e.g., within a threshold amount of time), the example medical exam distributor 102 is to escalate the medical exam and move the medical exam to the top of a radiologist workflow. For example, if a medical exam is to be conducted within one hour to maintain the time constraints of a service level agreement, the example medical exam distributor 102 moves the medical exam to a top position or queue of a radiologist workflow such that the radiologist will conduct the medical exam before conducting other medical exams.

In some examples, a load-balancing rule is used to increase a likelihood that a radiologist with sufficient experience is assigned to a medical exam associated with a relative value unit score. A relative value unit (RVU) score is a measure of value for practitioner services. A relative value unit score may be associated with a level of experience of a radiologist. For example, a medical exam with a high relative value unit score may be a more difficult exam to conduct and, thus, a more experienced radiologist is to conduct the exam. In some examples, a load-balancing rule defines that the example medical exam distributor is to remove a medical exam from a radiologist workflow if the radiologist does not have sufficient experience to conduct the medical exam based on a relative value unit score of the medical exam. Additional load-balancing rules can be defined based on network, institutional, and/or cross-intuitional workflow targets.

Figure 5:
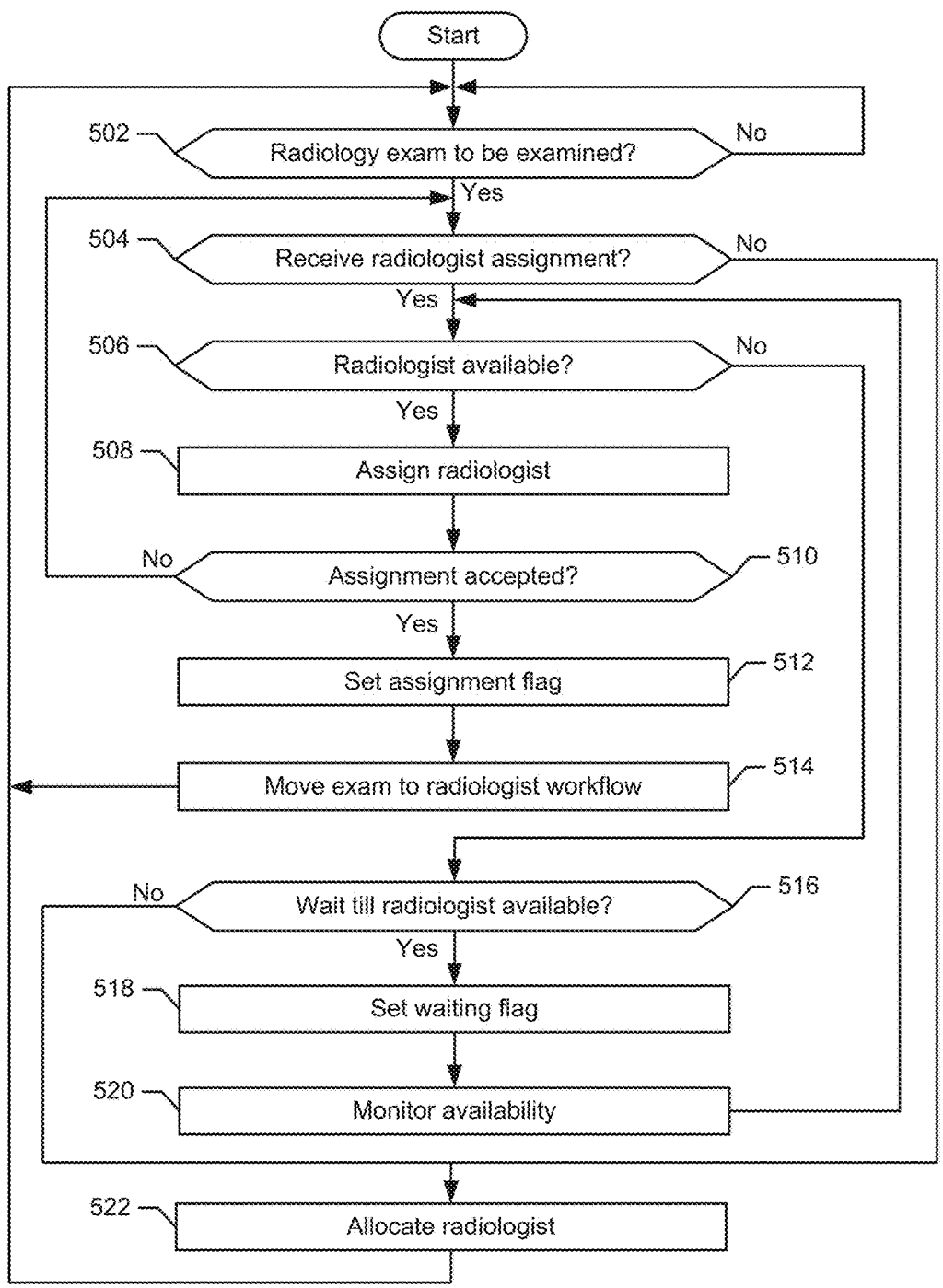
FIG. 5 illustrates a flow diagram illustrating an example method for assigning a radiologist at the example medical exam distributor of FIGS. 1 and/or 2.

FIG. 5 illustrates a flow diagram illustrating an example method for assigning a radiologist at the example medical exam distributor 102 of FIGS. 1 and/or 2. Initially, the example medical exam distributor 102 determines if a radiology exam is to be examined (block 502). Control remains at block 502 until a radiology exam is ready to be examined. The example medical exam distributor 102 then determines if a radiologist assignment has been received (block 504). For example, when a medical exam is to be examined, a practitioner (e.g., an attending) can assign the medical exam to another radiologist (e.g., a resident). If a radiologist assignment has not been received, control proceeds to block 522, and the example medical exam distributor 102 allocates the medical exam to a radiologist (e.g., the system automatically selects a radiologist and moves the medical exam to the selected radiologist's workflow) (block 522). An example method to allocate a medical exam is discussed below in connection with FIG. 6.

If a radiologist assignment has been received, the example medical exam distributor 102 determines if the radiologist is available to examine the medical exam using, for example, the profile of the assigned radiologist (block 506). For example, if the profile of the radiologist specifies that the radiologist is at Hospital A, and the medical exam to be assigned is at Hospital B, the radiologist is not available to be assigned to the medical exam.

If the radiologist is available, the example medical exam distributor 102 assigns the medical exam to the radiologist (block 508). The example medical exam distributor 102 notifies the radiologist of the exam assignment and determines if the radiologist has accepted the exam assignment (block 510).

If the radiologist declines the assignment, the medical exam is assigned to another radiologist (block 504). If the medical exam is not assigned to another radiologist (e.g., if a practitioner does not select another radiologist to take the exam), the example medical exam distributor 102 allocates the medical exam to a radiologist (block 522). In certain examples, the radiologist to whom the exam is allocated is the same radiologist who refused the assignment.

If the radiologist accepts the exam assignment, the example medical exam distributor sets an assignment flag (block 512) and moves the medical exam to the radiologist's workflow (block 514). Moving the medical exam to the radiologist's workflow removes the medical exam from the group of medical exams that have not yet been assigned and/or allocated to a radiologist. The assigned medical exam will be visible in the radiologist's workflow to enable the radiologist to conduct the exam when the assigned medical exam is at the top of the workflow queue.

If the radiologist is not available, the assigning practitioner specifies whether to wait till the desired radiologist is available to assign the medical exam to the desired radiologist (block 516). If the assigning practitioner wishes to wait till the desired radiologist is available, the example medical exam distributor 102 sets a waiting flag (block 518), and monitors the availability of the desired radiologist (block 520). Once the desired radiologist is available (block 506), the example medical exam distributor 102 assigns the desired radiologist to the medical exam (block 508). If the assigning practitioner does not wish to wait till the desired radiologist is available (block 516), the example medical exam distributor 102 allocates the medical exam to another radiologist (e.g., the system automatically selects a radiologist and moves the medical exam to the selected radiologist's workflow) (block 522). Control then returns to block 502 to determine if another radiology exam is to be examined.

Figure 6:
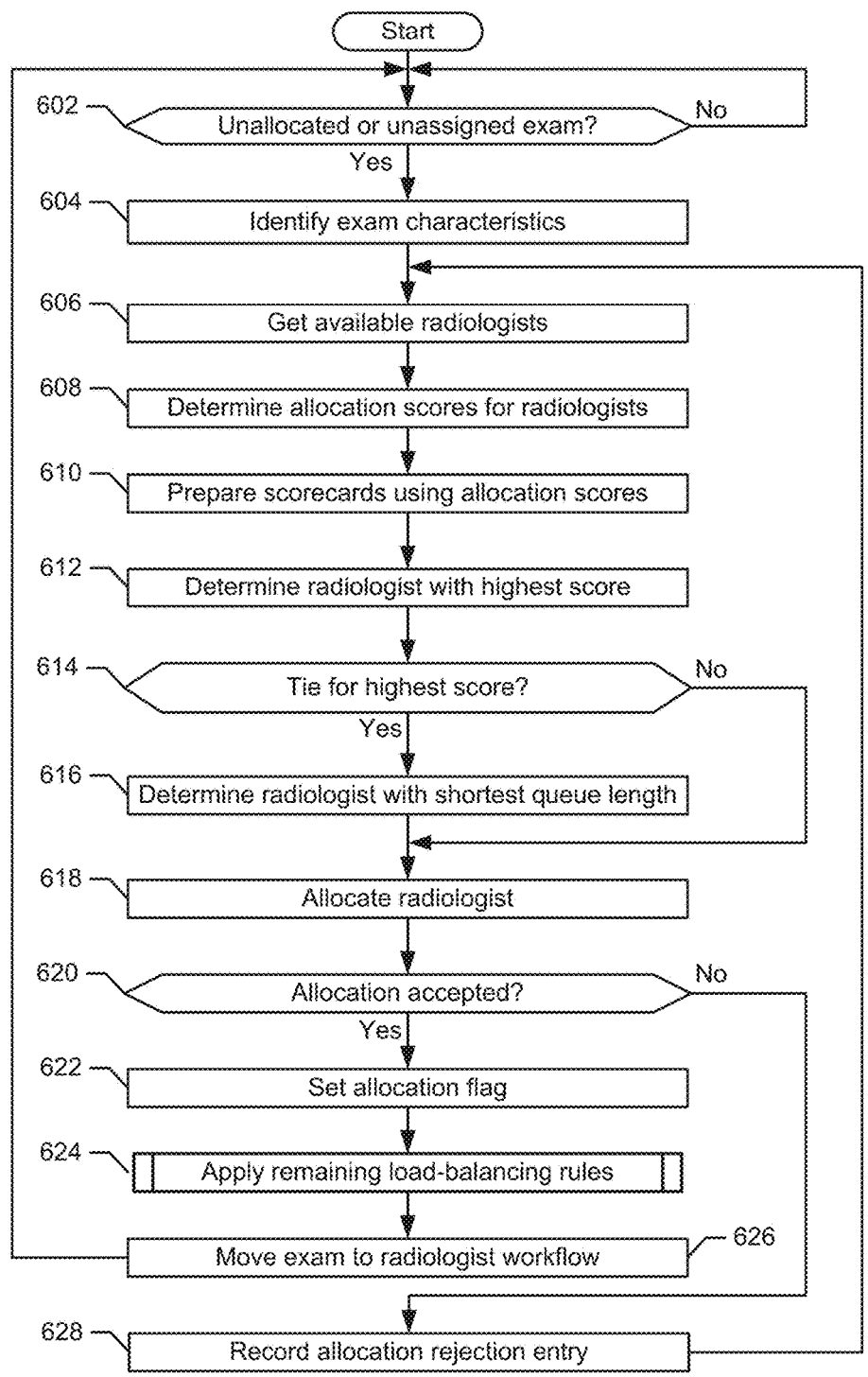
FIG. 6 illustrates a flow diagram illustrating an example method for allocating a radiologist at the example medical exam distributor of FIGS. 1 and/or 2.

FIG. 6 illustrates a flow diagram illustrating an example method for allocating a radiologist at the example medical exam distributor 102 of FIGS. 1 and/or 2. Initially, the example medical exam distributor 102 determines if there is a medical exam that has not been assigned and/or has not been allocated (block 602). For example, a medical exam is to be allocated to a radiologist when the medical exam has not been assigned by a practitioner to a radiologist, and has not yet been automatically assigned to a radiologist. Control remains at block 602 until there is an unallocated and/or unassigned exam.

Once there is an unallocated and/or unassigned exam, the example medical exam distributor 102 identifies exam characteristics of the medical exam to be allocated (block 604). Exam characteristics include, for example, location, experience level, specialty, modality, and/or body part associated with the medical exam to be allocated. The example medical exam distributor 102 identifies available radiologists (block 606). The example medical exam distributor 102 identifies available radiologist using radiologist profiles (e.g., if the radiologist is at the same location as the medical exam to be allocated, the radiologist is available to perform the medical exam). In some examples, a radiologist indicates that he is available or not available (e.g., using a status indicator via the example user interface 226 of FIG. 2). For example, the radiologist can indicate that he is unavailable to perform medical exams if he is currently conducting a medical exam, if he is scheduled to attend a meeting, etc. Once the example medical exam distributor 102 determines the available radiologists (e.g., radiologists capable of performing the medical exam to be allocated), the example medical exam distributor 102 determines allocation scores for the available radiologists (block 608). The example medical exam distributor 102 uses the matching rules and point values defined using, for example, the method of FIG. 4 to calculate allocations scores to determine a radiologist that best matches the medical exam to be allocated. An example method to determine an allocation score is described below in connection with FIG. 7.

To compare allocations scores for available radiologists and determines the best match, the example medical exam distributor 102 prepares scorecards for each of the available radiologists using the allocation scores (block 610). Example scorecards identify the radiologist, the overall allocation score of the radiologist, and each of the point values allocated to the radiologist that make up the overall allocation score (e.g., points allocated to the radiologist for the location, experience level, specialty, modality, and/or body part). The scorecards can be viewed by a practitioner (e.g., via the user interface 226 of FIG. 2) to see how well a radiologist matches a medical exam to be allocated. An example scorecard is illustrated in FIG. 11.

The example medical exam distributor 102 determines the available radiologist with the highest allocation score (block 612). The example medical exam distributor 102 determines if more than one radiologist has the highest allocation score (e.g., if there was a tie between allocation scores) (block 614). If a particular radiologist has the highest allocation score (e.g., a single allocation score is the highest allocation score), the example medical exam distributor 102 allocates the medical exam to the radiologist with the highest allocation score (block 618). If more than one radiologist has the highest allocation score (e.g., if there is a tie between allocation scores), the example medical exam distributor 102 determines the radiologist with the highest allocation score and the shortest workflow queue length (block 616). For example, a first and a second radiologist may both obtain an allocation score of twelve, but the first radiologist may have a queue length of three while the second radiologist has a queue length of four. The example medical exam distributor 102 allocates the medical exam to the radiologist with the highest allocation score and the shortest workflow queue length (e.g., the first radiologist) (block 618) so that the medical exam will be examined more quickly than if the medical exam was allocated to a radiologist with a longer queue length.

The example medical exam distributor 102 then determines if the exam allocation has been accepted by the radiologist (block 620). If the radiologist accepts the allocation of the medical exam, the example medical exam distributor 102 sets an allocation flag (block 622) In some examples, the example medical exam distributor 102 optionally applies any remaining relevant load-balancing rules to determine if any changes are to be made to the exam allocation and/or the radiologist workflow to facilitate compliance with hospital standards, to meet efficiency goals, and/or to respond to user feedback (block 624). An example method for applying load-balancing rules is described below in connection with FIG. 8. The example medical exam distributor 102 moves the medical exam to the radiologist's workflow (block 626). Moving the medical exam to the radiologist's workflow enables the radiologist to conduct the medical exam when the medical exam reaches the top of the workflow queue.

If the radiologist declines the allocation of the medical exam (block 620), the example medical exam distributor 102 records an allocation rejection entry for the radiologist (block 628). The example medical exam distributor 102 maintains logs of rejections of exam allocations by radiologists so that a practitioner or administrator can review such rejections. For example, if a radiologist is declining numerous exam allocations and/or a particular type of exam allocation, a practitioner (e.g., an attending) may wish to review this information (e.g., so that the practitioner may intervene). Control then returns to block 602 to determine if another medical exam has yet to be assigned and/or allocated.

Figure 7:
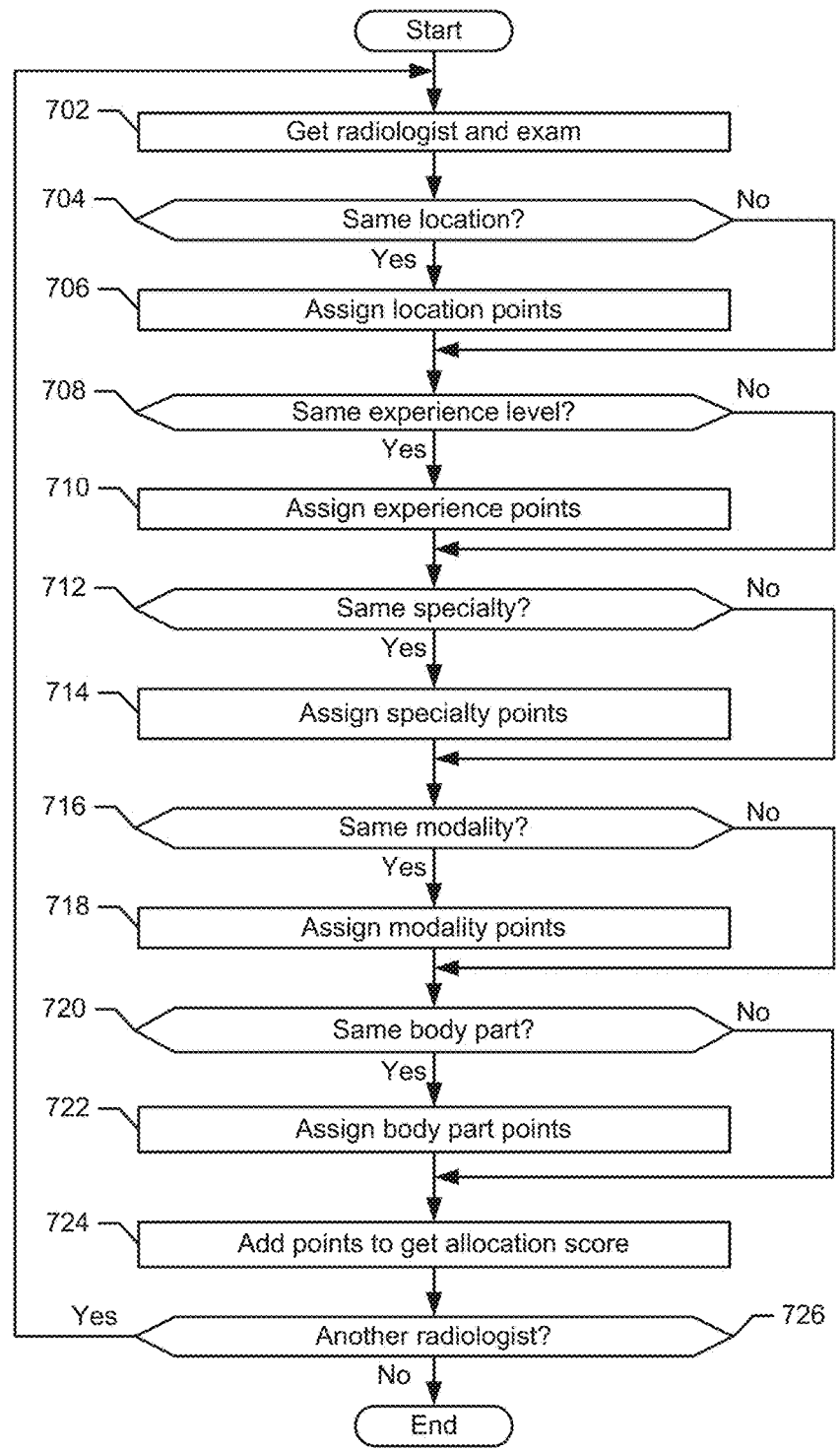
FIG. 7 illustrates a flow diagram illustrating an example method for determining allocation scores at the example medical exam distributor of FIGS. 1 and/or 2.

FIG. 7 illustrates a flow diagram illustrating an example method for determining allocation scores at the example medical exam distributor 102 of FIGS. 1 and/or 2. To determine a best match for a medical exam to be allocated, the example medical exam distributor 102 determines an allocation score for each available radiologist for the medical exam. Initially, the example medical exam distributor 102 identifies an available radiologist and a medical exam to be allocated (e.g., using the method of FIG. 6) (block 702). To determine an allocation score, the example medical exam distributor 102 assigns point values for each characteristic associated with a radiologist that matches a characteristic of the medical exam to be allocated. The example medical exam distributor 102 determines if the medical exam is at a location that is the same as the radiologist (block 704). If the medical exam is not at a location that is the same as the radiologist, control proceeds to block 708. If the medical exam is at a location that is the same as the radiologist, the example medical exam distributor 102 assigns and/or allocates a location point value to the radiologist (e.g., which has been previously defined using the method of FIG. 4) (block 706).

The example medical exam distributor 102 determines if an experience level associated with the medical exam (e.g., an experience level needed by a practitioner to conduct the medical exam) is the same as an experience level of the radiologist (block 708). If the experience level associated with the medical exam is not the same as an experience level of the radiologist, control proceeds to block 712. If the experience level associated with the medical exam is the same as an experience level of the radiologist, the example medical exam distributor 102 assigns and/or allocates an experience point value to the radiologist (block 710).

The example medical exam distributor 102 determines if a specialty associated with the medical exam is the same as a specialty associated with the radiologist (block 712). If the specialty associated with the medical exam is not the same as a specialty associated with the radiologist, control proceeds to block 716. If the specialty associated with the medical exam is the same as a specialty associated with the radiologist, the example medical exam distributor 102 assigns and/or allocates a specialty point value to the radiologist (block 714).

The example medical exam distributor 102 determines if a modality associated with the medical exam is the same as a modality associated with the radiologist (block 716). If a modality associated with the medical exam is not the same as a modality associated with the radiologist, control proceeds to block 720. If a modality associated with the medical exam is the same as a modality associated with the radiologist, the example medical exam distributor 102 assigns and/or allocates a modality point value to the radiologist (block 718).

The example medical exam distributor 102 determines if a body part associated with the medical exam is the same as a body part associated with the radiologist (block 720). If a body part associated with the medical exam is not the same as a body part associated with the radiologist, control proceeds to block 724. If a body part associated with the medical exam is the same as a body part associated with the radiologist, the example medical exam distributor 102 assigns and/or allocates a body part point value to the radiologist (block 722).

The example medical exam distributor 102 totals the point values assigned and/or allocated to the radiologist to determine the overall allocation score (block 724). The example medical exam distributor 102 determines if there is another available radiologist for whom to determine an allocation score (block 726). The example medical exam distributor 102 determines allocation scores for each available radiologist so that the allocation scores can be compared and a best match for the medical exam can be determined. If there is another available radiologist, control returns to block 702, and the radiologist is examined. If there is not another available radiologist, the example method of FIG. 7 ends.

Figure 8:
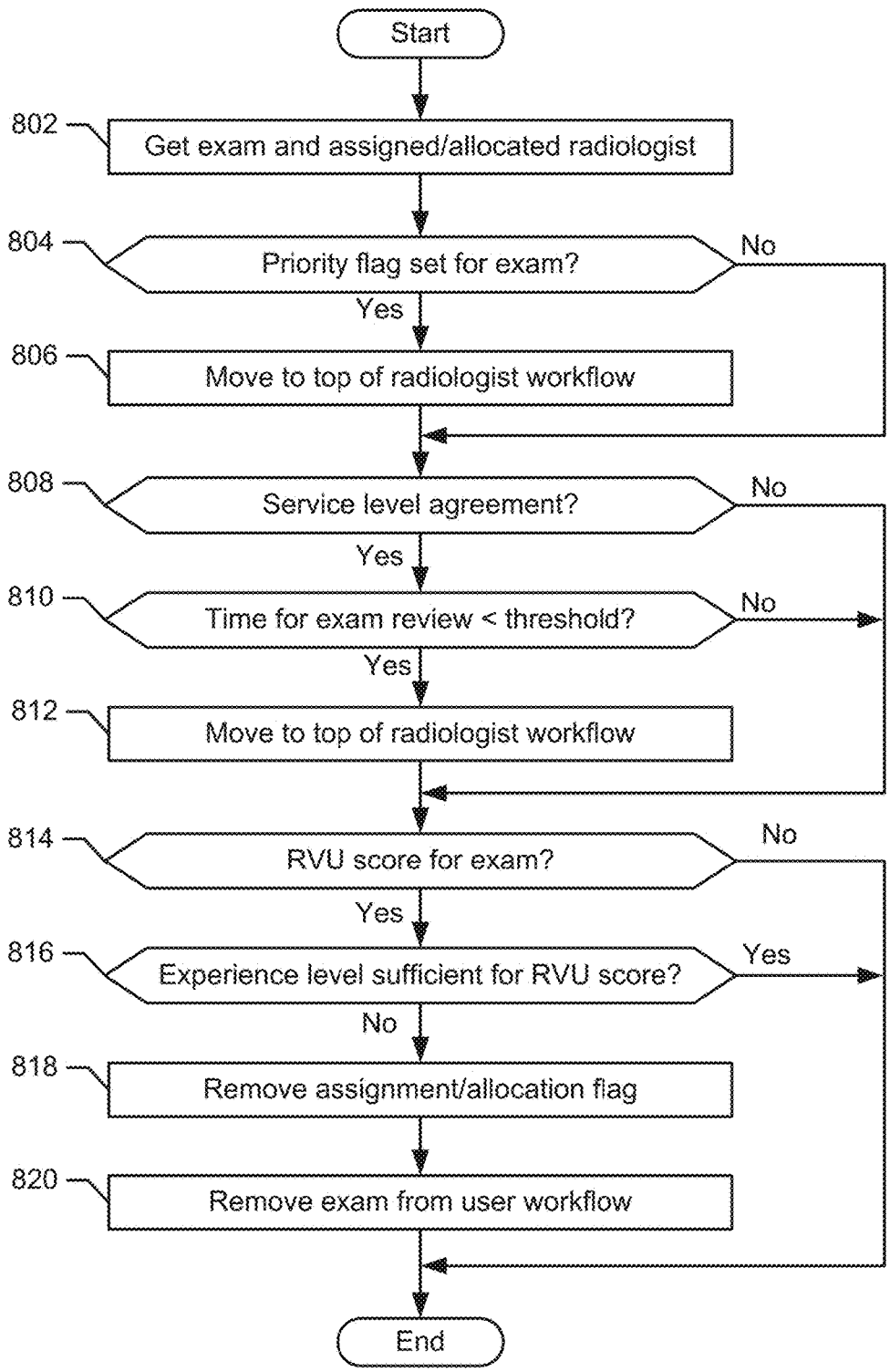
FIG. 8 illustrates a flow diagram illustrating an example method for applying load-balancing rules at the example medical exam distributor of FIGS. 1 and/or 2.

FIG. 8 illustrates a flow diagram illustrating an example method for applying load-balancing rules at the example medical exam distributor 102 of FIGS. 1 and/or 2. In some examples, load-balancing rules are applied to distribute an exam to a radiologist. In other examples, as shown in FIG. 8, the load-balancing rules are applied and/or reapplied once a medical exam has been assigned and/or allocated to a radiologist as part of, for example, ongoing monitoring and optimization of the exam distribution by the exam distributor 102. In some examples, load-balancing rules are used to increase the efficiency of the exam assignment and/or allocation process and/or the exam review process. For example, if a radiologist is interrupted such that his workstation is idle for a period of time and/or his work queue is increasing, the exam distributor 102 automatically re-evaluates the distribution of exams and applies the load-balancing to, for example, prioritize an exam in the radiologist's work queue and/or assign an exam to another radiologist.

Initially, the example medical exam distributor 102 accesses the medical exam and the assigned and/or allocated radiologist (block 802). The example medical exam distributor 102 determines if a priority flag has been set for the medical exam (block 804). If a priority flag has not been set, control proceeds to block 808. If a priority flag has been set, the example medical exam distributor 102 moves the medical exam to the top of the radiologist's workflow (e.g., so that the medical exam will be conducted prior to other medical exams in the workflow) (block 806).

The example medical exam distributor 102 determines if there is a service level agreement associated with the medical exam (block 808). If there is not a service level agreement associated with the medical exam, control proceeds to block 814. If there is a service level agreement associated with the medical exam, the example medical exam distributor 102 determines if there is sufficient time to perform the medical exam before the expiry of the time period defined in the service level agreement (e.g., if the time to perform the exam review is less than a threshold) (block 810). If there is sufficient time to perform the medical exam, control proceeds to block 814. If there is not sufficient time to perform the medical exam, the example medical exam distributor 102 moves the medical exam to the top of the radiologist's workflow (block 812).

The example medical exam distributor 102 determines if there is a relative value unit score associated with the medical exam (block 814). If there is not a relative value unit score associated with the medical exam, the example method of FIG. 8 ends. If there is a relative value unit score associated with the medical exam, the example medical exam distributor 102 determines if an experience level of the radiologist is sufficient for the relative value unit score of the medical exam (block 816). For example, a medical exam with a particular relative value unit score may require the exam to be performed by a practitioner with a particular level of experience. If the experience level of the assigned and/or allocated radiologist is sufficient for the relative value unit score, the example method of FIG. 8 ends. If the experience level of the assigned and/or allocated radiologist is not sufficient for the relative value unit score of the medical exam, the example medical exam distributor 102 removes the assignment and/or allocation flag for the radiologist (block 818) and removes the medical exam from the radiologist's workflow (block 820). The medical exam is then be assigned and/or allocated to another radiologist. The example method of FIG. 8 then ends.

Figure 9:
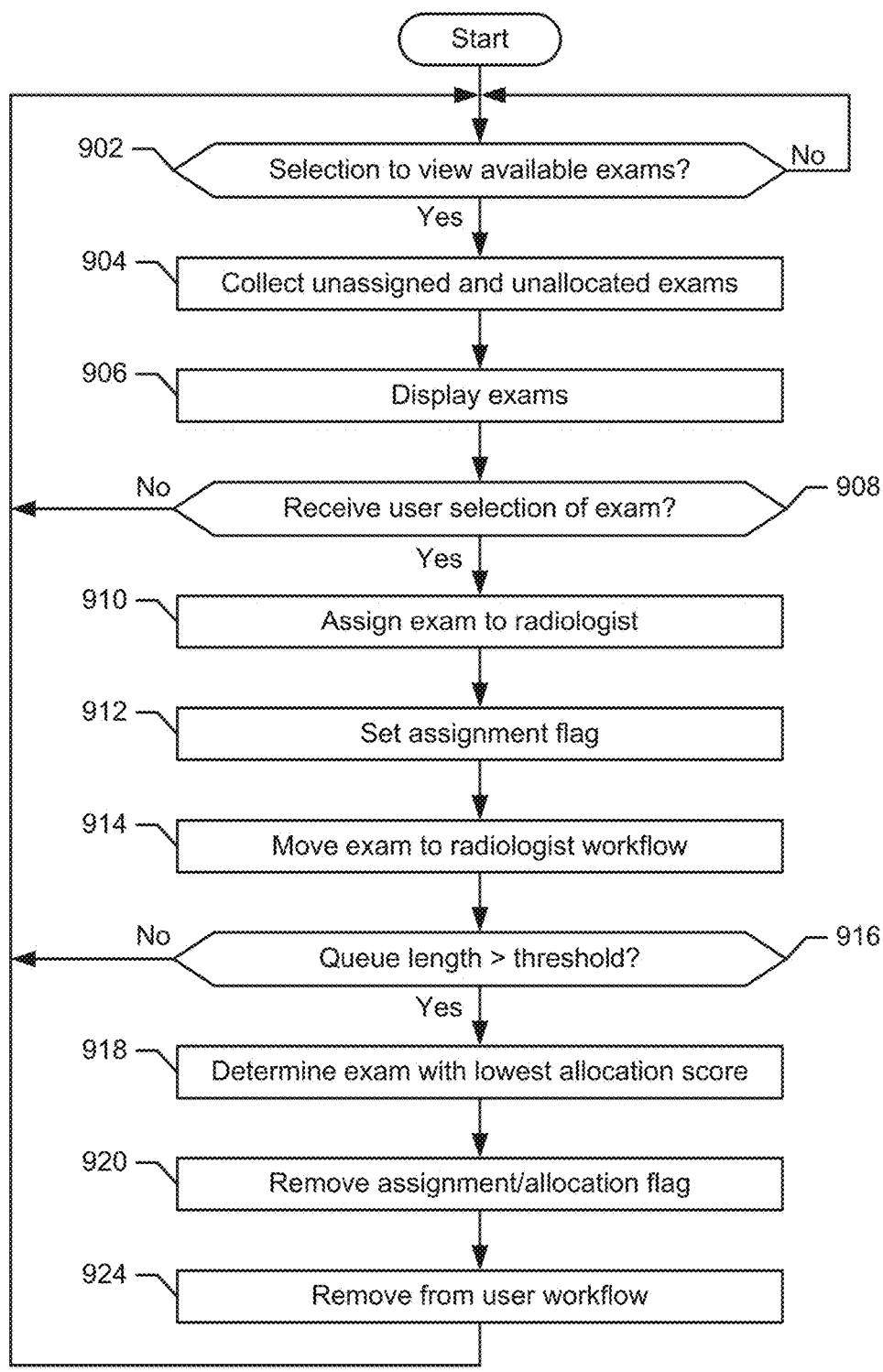
FIG. 9 illustrates a flow diagram illustrating another example method for assigning a radiologist at the example medical exam distributor of FIGS. 1 and/or 2.

FIG. 9 illustrates a flow diagram illustrating another example method for assigning a radiologist at the example medical exam distributor 102 of FIGS. 1 and/or 2. In some examples, a radiologist assigns an available medical exam to himself. Initially, the example medical exam distributor 102 determines if a selection has been made by a user to view available exams (e.g., exams that have not yet been allocated and/or assigned) (block 902). Control remains at block 902 until a selection to view available exams has been made.

Once a user has selected to view available exams, the example medical exam distributor 102 collects medical exams that have not yet been assigned and/or allocated (block 904). The example medical exam distributor 102 displays the available medical exams for the user via, for example, the user interface 226 of FIG. 2. The example medical exam distributor 102 determines if a user has selected an available medical exam for assignment (block 908). If the user does not select an exam for assignment, control returns to block 902. If a user selects an available exam for assignment, the example medical exam distributor 102 assigns the exam to the selecting radiologist (block 910). The example medical exam distributor 102 sets an assignment flag (block 912) and moves the medical exam to the radiologist's workflow (block 914).

The example medical exam distributor 102 determines if a queue length of the radiologist's workflow exceeds a threshold queue length (e.g., it is determined if the newly selected medical exam causes the workflow to be too long) (block 916). If the queue length of the radiologist's workflow exceeds the threshold queue length (e.g., which can be defined using the example method of FIG. 4), the example medical exam distributor determines the medical exam in the workflow that has the lowest allocation score (e.g., using the allocation scorecards) (block 918). The example medical exam distributor removes the assignment and/or allocation flag for the medical exam with the lowest allocation score (block 920), and removes the medical exam from the radiologist's workflow (block 924). The removed medical exam can then be assigned and/or allocated to another radiologist. Control then returns to block 902.

In operation, a radiologist accesses a medical exam workflow via, for example, a user interface (e.g., the user interface 226 of FIG. 2) at a workstation (e.g., the workstation 214 of FIG. 2). The medical exam workflow includes a work queue of medical exams for the radiologist to perform. The medical exams in the work queue are assigned and/or allocated to the radiologist by the example medical exam distributor 102.

For example, a medical exam in the work queue may have been assigned to the radiologist by himself. In such an example, the radiologist accessed a listing of available medical exams (e.g., medical exams not yet assigned and/or allocated to a radiologist), determined a medical exam the radiologist would like to perform, and then selected the medical exam. Once the radiologist selected the medical exam, the example medical exam distributor 102 assigned the medical exam to the radiologist, and moved the medical exam to the radiologist's workflow. The example medical exam distributor 102 provides an indication in the workflow that this medical exam has been assigned to the radiologist.

In some examples, a medical exam in the work queue was assigned to the radiologist by another radiologist (e.g., a supervisor). In such an example, the supervisor accessed a listing of available medical exams (e.g., medical exams not yet assigned and/or allocated to a radiologist), determined a medical exam and radiologist the supervisor would like to assign, and then selected the medical exam and the radiologist to perform the exam. Once the supervisor selected the medical exam, the example medical exam distributor 102 assigned the medical exam to the radiologist, and moved the medical exam to the radiologist's workflow. The example medical exam distributor 102 provides an indication in the workflow that this medical exam has been assigned to the radiologist, who assigned the medical exam, etc. In some examples, a medical exam in the work queue was allocated to the radiologist by the example medical exam distributor 102. In such an example, the medical exam distributor 102 accessed an available medical exam and determined a radiologist that would best match the medical exam. To determine the best match, the example medical exam distributor 102 compared characteristics of the medical exam (e.g., location, experience level preferred, specialty, modality, body part, etc.) with profiles of available radiologists (e.g., which specify location of the radiologists, experience level of the radiologists, and specialties, modalities, and/or body parts preferred by the radiologists). The example medical exam distributor 102 assigned allocation scores to the available radiologists based on how well the exam characteristics match the radiologist profiles and allocated the medical exam to the radiologist with the highest score. The example medical exam distributor 102 moved the medical exam to the workflow of the radiologist with the highest allocation score. The radiologist (or other practitioner) can view the radiologist scores (e.g., via a scorecard interface) to see how and/or why the medical exam was allocated to the radiologist (e.g., the scores obtained by the radiologist illustrating that the radiologist was the best match for the medical exam).

In some examples, the radiologist can view the assigned and/or allocated medical exam and determine that he does not wish to accept the assignment and/or allocation. If the radiologist rejects the assignment and/or allocation of the medical exam, the example medical exam distributor 102 removes the medical exam from the radiologist's workflow, and assigns and/or allocates the medical exam to another radiologist. If the radiologist rejects the assignment and/or allocation of the medical exam, the example medical exam distributor 102 logs an entry of the exam rejection so that the radiologist's exam rejection activity can be monitored (e.g., by the supervisor).

In some examples, a medical exam is moved to a top position in the radiologist's workflow by the example medical exam distributor 102. For example, if the medical exam distributor 102 determines that a medical exam is a priority, the example medical exam distributor 102 moves the medical exam to the top of the radiologist's workflow such that the radiologist will conduct the medical exam when the radiologist exam becomes available (e.g., when the radiologist finishes an exam he is currently conducting). The example medical exam distributor 102 automatically prioritizes the radiologist's workflow without manipulation by the radiologist (e.g., the radiologist is not required to monitor the priority of medical exams in his workflow).

The example medical exam distributor 102 enables a radiologist to easily view and control a medical exam workflow. Using the example medical exam distributor 102, the radiologist can see what medical exams have been assigned to the radiologist, what exams have been allocated to the radiologist, why exam have been allocated to the radiologist, what exams have priority and are to be conducted before other exams, etc.

FIG. 10 illustrates an example interface 1000 created by the example medical exam distributor 102 of FIGS. 1 and/or 2. The example medical exam distributor 102 prepares the example interface 1000 to provide a user with a listing of medical exams and statuses associated with those medical exams (e.g., whether the exams have been assigned and/or allocated).

In the illustrated example, the example interface 1000 includes a listing of example patients 1002 and associated medical exams 1004. For example, Patient 2 is associated with Exam 2, indicating that Exam 2 is to be conducted by a radiologist on Patient 2. The example interface 1000 includes example assignment status indicators 1006, example allocation status indicators 1008, and example queue status indicators 1010. In the illustrated example, the assignment status indicators 1006 are used to indicate if an exam has been assigned to a radiologist. The example allocation status indicators 1008 are used to indicate if an exam has been allocated to a radiologist. The example queue status indicators 1010 are used to indicate if an exam has reached a top position of a workflow queue of a radiologist (e.g., indicating that the exam will be performed next). The example interface 1000 also includes a listing of radiologists 1012 that have been assigned and/or allocated to an exam.

In the illustrated example, Exam 2 has been assigned to Radiologist 2, and Exam 4 has been allocated to Radiologist 1 by the example medical exam distributor 102. Exam 4 is also at the top of the workflow associated with Radiologist 1 such that Radiologist 1 will perform the Exam 4 when the Radiologist 1 becomes available. In some examples, Exam 4 is selected to allow a user to view scorecards illustrating how the example medical exam distributor 102 determined the allocation of the Exam 4. An example scorecard interface is illustrated in FIG. 11.

FIG. 11 illustrates an example interface 1100 created by the example medical exam distributor 102 of FIGS. 1 and/or 2. The example interface 1100 illustrates example scorecards for a plurality of radiologists 1102 for the allocation of Exam 4 of FIG. 10. The example interface 1100 illustrates experience level point values 1104, specialty point values 1106, modality point values 1108, body part point values 1110, and total point values 1112 assigned to the plurality of radiologists 1102 during the medical exam allocation process for the Exam 4 to be allocated. The example medical exam distributor 102 allocates the Exam 4 to Radiologist 1 because Radiologist 1 has the highest total point value 1112 for the plurality of radiologists 1102.

Figure 12:
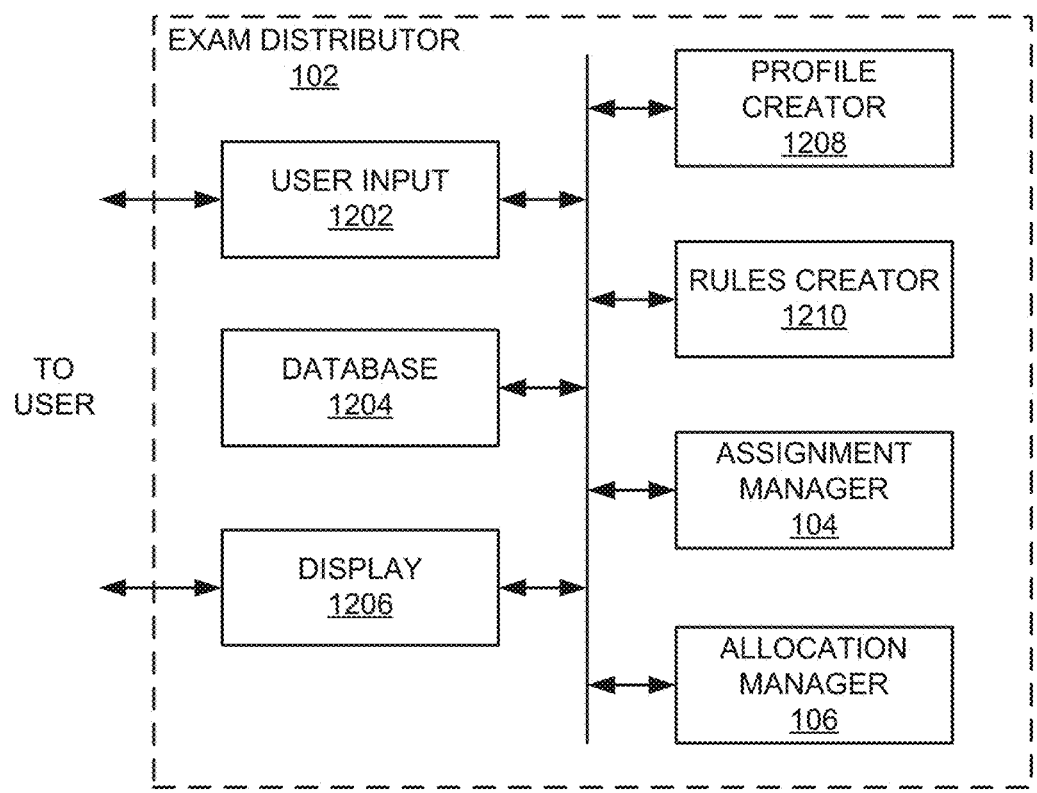
FIG. 12 shows a block diagram of the example medical exam distributor of FIGS. 1 and/or 2.

FIG. 12 shows a block diagram of the example medical exam distributor 102 of FIGS. 1 and/or 2. The example medical exam distributor 102 enables efficient assignment and/or allocation of medical exams to practitioners (e.g., radiologists) and management of practitioner workflows. The example medical exam distributor 102 of FIG. 12 includes an example user input 1202, an example database 1204, an example display 1206, an example profile creator 1208, an example rules creator 1210, the example assignment manager 104 of FIG. 1, and the example allocation manager 106 of FIG. 1.

The example database 1204 receives stores exam information, including patient and physician information, as well as information associated with the exam distributor 102, including, for example, radiologist profiles and load-balancing rules. In some examples, the database 1204 stores information associated with exams and radiologists at a healthcare institution, such as a hospital. In other examples, the database 1204 receives and stores exam and radiologist information for more than one healthcare institution. For example, several institutions (e.g., hospitals, outpatient facilities, etc.) may affiliate with respect to exam distribution and review such that a patient is examined at a first institution and a radiologist at a second institution is assigned to review the exam. In such examples, the database 1204 stores identifying information associated with the institution where the exam was performed to assist in the cross-enterprise distribution of exams.

The example profile creator 1208 creates profiles for radiologists to be used to assign and/or allocate medical exams to radiologists. The example profile creator 1208 receives input from a user via the example user input 1202 to identify a radiologist, an experience level of the radiologist (e.g., a resident, an attending, etc.), a specialty associated with the radiologist (e.g., emergency, pediatrics, etc.), a modality preferred by the radiologist (e.g., a computed tomography (CT) scan, a magnetic resonance imaging (MRI) exam, etc.), and/or a body part preferred by the radiologist (e.g., abdomen, chest, etc.). A radiologist profile also identifies days and/or times during which the radiologist practices with the preferred specialty, modality, and/or body part. For example, a radiologist may work in an emergency department on Mondays and Tuesdays, and may work in a pediatrics department on Wednesdays, Thursdays, and Fridays. A radiologist profile may also identify locations at which the radiologist practices the preferred specialty, modality, and/or body part. For example, a radiologist may work at Hospital A on Mondays and Tuesdays, and may work at Hospital B on Wednesdays, Thursdays, and Fridays. In some examples, the example profile creator 1208 creates multiple profiles for a radiologist. For example, if a radiologist works at different locations, and/or works on different specialties, modalities, and/or body parts at different days and/or times, the example profile creator 1208 creates a profile for the radiologist for each location, each day, and/or each time. The example profile creator 1208 stores the radiologist profiles at the example database 1204.

The example rules creator 1210 defines distribution rules to enable the assignment and/or allocation of medical exams. The example rules creator 1210 receives input from a user via the example user input 1202 to define the distribution rules. In some examples, automatic and/or default distribution rules are used by the example rules creator 1210. Also, in examples where the exams are received from more than one institution, the rules creator 1210 performs a mapping of identifiers associated with the exams and/or the healthcare institutions to standardize exam distribution between institutions. For example, factors such as exam modality, body part, radiologist specialty, and/or institution location are considered by the rules creator as part of defining load-balancing rules. Such mapping across affiliated institutions provides for consistency in applying the load-balancing rules and benchmarks for comparing workload information between radiologists at different institutions.

Distribution rules include queue length rules, matching rules, priority rules, and/or other load-balancing rules defined by exam and/or radiologist attributes. In some examples, a queue length rule defines a length of a radiologist workflow. For example, a queue length rule defines that a radiologist workflow comprises a queue length of five (e.g., a maximum of five exams may be assigned and/or allocated to a radiologist at one time).

In some examples, matching rules define how radiologists are to be matched with a medical exam to be distributed. A medical exam to be distributed is associated with a specialty, a modality, and/or a body part. In some examples, a matching rule defines that a radiologist is to be matched with a medical exam when a specialty associated with the radiologist matches a specialty associated with the medical exam, when a modality associated with the radiologist matches a modality associated with the medical exam, and/or when a body part associated with the radiologist matches a body part associated with the medical exam. Matching rules also define point values associated with a specialty match, a modality match, and/or a body part match. Point values are used to weight the matching process so that, for example, a match in a specialty is given more weight than a match in a body part. For example, a match between a specialty associated with a radiologist and a specialty associated with a medical exam may afford the radiologist ten (10) points. A match between a modality associated with a radiologist and a modality associated with a medical exam may afford the radiologist five (5) points. A match between a body part associated with a radiologist and a body part associated with a medical exam may afford the radiologist two (2) points.

In some examples, a priority rule defines that a medical exam marked with a priority flag is to be moved to a top position or queue of a radiologist workflow such that the radiologist will conduct the medical exam before conducting other medical exams. For example, a radiologist may determine that a medical exam is urgent and mark the exam with a priority flag. The medical exam is then moved to the top of the radiologist workflow. The distribution rules defined by the example rules creator 1210 are stored at the example database 1204.

In some examples, load-balancing rules are used to increase the efficiency of the exam assignment and/or allocation process and/or the exam review process. In some examples, a load-balancing rule is used to increase a likelihood that a service level agreement associated with a patient and/or a healthcare provider is met. For example, a service level agreement can include a length of time during which a medical exam is to be conducted. In such an example, a load-balancing rule defines that if the length of time during which a medical exam is to be conducted is approaching (e.g., within a threshold amount of time), the medical exam is to be escalated and moved to the top of a radiologist workflow. For example, if a medical exam is to be conducted within one hour to maintain the time constraints of a service level agreement, the medical exam will be moved to a top position or queue of a radiologist workflow such that the radiologist will conduct the medical exam before conducting other medical exams.

In some examples, a load-balancing rule is used to increase a likelihood that a radiologist with sufficient experience is assigned to a medical exam associated with a relative value unit score. A relative value unit (RVU) score is a measure of value for practitioner services. A relative value unit score may be associated with a level of experience of a radiologist. For example, a medical exam with a high relative value unit score may be a more difficult exam to conduct and, thus, a more experienced radiologist is to conduct the exam. In some examples, a load-balancing rule defines that a medical exam is to be removed from a radiologist workflow if the radiologist does not have sufficient experience to conduct the medical exam based on a relative value unit score of the medical exam.

The example assignment manager 104 assigns medical exams to radiologists automatically and/or in response to user input. In some examples, the assignment manager 104 assigns exams automatically based on the matching rules, the priority rules, and/or, more generally, the load-balancing rules defined by the rules creator 1210. In some examples, the automatic assignment is based on a radiologist's schedule. For example, the example assignment manager 104 determines if the assigned radiologist is available to examine the medical exam using, for example, the profile of the assigned radiologist stored at the example database 1204. For example, if the profile of the assigned radiologist specifies that the radiologist is at Hospital A, and the medical exam to be assigned is at Hospital B, the radiologist is not available to be assigned to the medical exam. In some examples, a radiologist indicates if he is available or not. If the radiologist is available, the example assignment manager 104 assigns the medical exam to the radiologist.

In some examples, the assignment manager 104 assigns the exam to the examiner in response to instructions received from, for example, the assigning practitioner. For example, if the preferred radiologist is not available, the assigning practitioner specifies whether to wait till the desired radiologist is available to assign the medical exam to the desired radiologist or assigns the exam to the offline radiologist. If the assigning practitioner wishes to wait till the desired radiologist is available, the example assignment manager sets a waiting flag, and monitors the availability of the desired radiologist. Once available, the example assignment manager 104 assigns the desired radiologist to the medical exam. If the assigning practitioner does not wish to wait till the desired radiologist is available, the example allocation manager 106 allocates the medical exam to another radiologist (e.g., the example allocation manager 106 automatically selects a radiologist and moves the medical exam to the selected radiologist's workflow). If the assigning practitioner prefers to assign the exam to the offline radiologist, the assignment manager 104 assigns the medical exam to the radiologist in response to a corresponding input from the assigning practitioner. Thus, the assignment manager 104 responds to manual instructions provided by an administrator.

In other examples, the assignment manager 104 assigns the medical exam to a radiologist requested by a referring physician. For example, a referring physician can request a radiologist based on exam attributes, such as body part, modality, and/or difficulty level, and/or based on a relationship with the specific radiologist. In such examples, the exam distributor 102 assigns the exam to the preferred radiologist. In other examples, the exam distributor 102 applies the load-balancing rules to assign the exam to another qualified radiologist if, for example, the preferred radiologist is not available.

In some examples, the radiologist accepts the assignment (e.g., via the user input 1202). If the radiologist accepts the assignment of the medical exam, the example assignment manager 104 sets an assignment flag, and moves the medical exam to the radiologist's workflow. In some examples, the radiologist declines the assignment. For example, a radiologist may have a full workflow and, thus, may not want to add the medical exam being assigned (e.g., which may require removing another medical exam in the radiologist's workflow). If the radiologist declines the assignment, the example assignment manager 104 assigns the medical exam to another radiologist (e.g., if a user selects another radiologist for assignment). If the medical exam is not assigned to another radiologist (e.g., if a practitioner does not select another radiologist to take the exam), the example allocation manager 106 allocates the medical exam to a radiologist.

In some examples, a radiologist assigns an available medical exam to himself via the example user input 1202. For example, the assignment manager 104 collects unassigned and/or unallocated exams to be displayed for a radiologist via the example display 1206. Unassigned and/or unallocated exams are stored at, for example, the database 1204. The radiologist can view the medical exams and select a particular medical exam he wishes to perform via the example user input 1202. The example assignment manager 104 assigns the exam to the radiologist, sets an assignment flag, and moves the selected medical exam to the radiologist's workflow. The example assignment manager 104 also determines if a queue length of the radiologist's workflow exceeds a threshold queue length (e.g., it is determined if the newly selected medical exam causes the workflow to be too long). If the queue length of the radiologist's workflow exceeds the threshold queue length, the example assignment manager 104 determines the medical exam in the workflow that has the lowest allocation score (e.g., using the allocation scorecards). The example assignment manager 104 removes the assignment and/or allocation flag for the medical exam with the lowest allocation score, and removes the medical exam from the radiologist's workflow.

In some examples, the assignment manager 104 reviews and processes the assignment status of exams in response to a discrete activity detected by the assignment manager, such as a new exam received by the exam distributor 102 or a decision by a radiologist to reject an exam assignment. In other examples, the assignment manager 104 reviews the exams in a batch configuration. In such examples, the assignment manager 104 applies the load-balancing rules to one or more exams requiring review at predetermined intervals such that exams are assigned and distributed in batches.

The example allocation manager 106 allocates medical exams to radiologists. For example, the allocation manager 106 allocates a medical exam to a radiologist when the medical exam has not been assigned by a practitioner to a radiologist, and has not yet been automatically assigned to a radiologist. To allocate a medical exam, the example allocation manager 106 identifies exam characteristics of the medical exam. Exam characteristics include, for example, location, experience level, specialty, modality, and/or body part associated with the medical exam to be allocated. The example allocation manager 106 identifies available radiologists and uses the matching rules and point values to determine a radiologist that best matches the medical exam to be allocated.

To determine a best match for the medical exam to be allocated, the example allocation manager 106 determines an allocation score for each available radiologist for the medical exam. To determine an allocation score, the example allocation manager assigns point values for each characteristic associated with a radiologist that matches a characteristic of the medical exam. For example, if the medical exam is at a location that is the same as the radiologist, the example allocation manager 106 assigns and/or allocates a location point value (e.g., which has been previously specified during the defining of the matching rules) to the radiologist. If an experience level associated with the medical exam (e.g., an experience level needed by a practitioner to conduct the medical exam) is the same as an experience level of the radiologist, the example allocation manager 106 assigns and/or allocates an experience point value to the radiologist. If a specialty associated with the medical exam is the same as a specialty associated with the radiologist, the example allocation manager 106 assigns and/or allocates a specialty point value to the radiologist. If a modality associated with the medical exam is the same as a modality associated with the radiologist, the example allocation manager 106 assigns and/or allocates a modality point value to the radiologist. If a body part associated with the medical exam is the same as a body part associated with the radiologist, the example allocation manager 106 assigns and/or allocates a body part point value to the radiologist. The example allocation manager 106 totals the point values assigned and/or allocated to the radiologist to determine the overall allocation score. The example allocation manager 106 determines allocation scores for each available radiologist so that the allocation scores can be compared.

To compare allocations scores for available radiologists, the example allocation manager 106 prepares scorecards for each of the available radiologists using the allocation scores. Example scorecards identify the radiologist, the overall allocation score of the radiologist, and each of the point values allocated to the radiologist that make up the overall allocation score. The scorecards can be viewed by a practitioner via the example display 1206 to see how well a radiologist matches a medical exam to be allocated.

The example allocation manager 106 determines the available radiologist with the highest allocation score. If a particular radiologist has the highest allocation score (e.g., a single allocation score is the highest allocation score), the example allocation manager 106 allocates the medical exam to the radiologist with the highest allocation score. If more than one radiologist has the highest allocation score (e.g., if there is a tie between allocation scores), the example allocation manager 106 determines the radiologist with the highest allocation score and the shortest workflow queue length. For example, a first and a second radiologist can both obtain an allocation score of twelve, but the first radiologist may have a queue length of three while the second radiologist has a queue length of four. The example allocation manager 106 allocates the medical exam to the radiologist with the highest allocation score and the shortest workflow queue length (e.g., the first radiologist) so that the medical exam will be examined more quickly than if the medical exam was allocated to a radiologist with a longer queue length.

In some examples, a radiologist accepts or declines the allocation of the medical exam via the example user input 1202. If the radiologist accepts the allocation of the medical exam, the example allocation manager 106 sets an allocation flag and moves the medical exam to the radiologist's workflow. If the radiologist declines the allocation of the medical exam, the example allocation manager 106 records an allocation rejection entry for the radiologist. The example allocation manager 106 maintains logs of rejections of exam allocations by radiologists so that a practitioner can review such rejections. For example, if a radiologist is declining numerous exam allocations and/or a particular type of exam allocation, a practitioner (e.g., an attending) may wish to review this information (e.g., so that the practitioner may intervene).

The example allocation manager 106 also applies load-balancing rules once a medical exam has been assigned and/or allocated to a radiologist. Load-balancing rules are used to increase the efficiency of the exam assignment and/or allocation process and/or the exam review process. In some examples, the example allocation manager 106 determines if a priority flag has been set for a medical exam. If a priority flag has been set, the example allocation manager 106 moves the medical exam to the top of the radiologist's workflow (e.g., so that the medical exam will be conducted prior to other medical exams in the workflow). If there is a service level agreement associated with the medical exam, the example allocation manager 106 determines if there is sufficient time to perform the medical exam before the expiry of the time period defined in the service level agreement. If there is not sufficient time to perform the medical exam, the example allocation manager 106 moves the medical exam to the top of the radiologist's workflow.

If there is a relative value unit score associated with the medical exam, the example allocation manager 106 determines if the experience level of the radiologist is sufficient for the relative value unit score of the medical exam. For example, a medical exam with a particular relative value unit score may require the exam to be performed by a practitioner with a particular level of experience. If the experience level of the assigned and/or allocation radiologist is not sufficient for the relative value unit score of the medical exam, the example allocation manager 106 removes an assignment and/or allocation flag for the radiologist so that the medical exam is removed from the radiologist's workflow. The medical exam can then be assigned and/or allocated to another radiologist by the example assignment manager 104 and/or the example allocation manager 106.

While an example manner of implementing the medical exam distributor 102 of FIGS. 1 and/or 2 is illustrated in FIG. 12, one or more of the elements, processes and/or devices illustrated in FIG. 12 can be combined, divided, re-arranged, omitted, eliminated and/or implemented in any other way. Further, the example user input 1202, the example database 1204, the example display 1206, the example profile creator 1208, the example rules creator 1210, the example assignment manager 104, the example allocation manager 106, and/or, more generally, the example medical exam distributor 102 of FIG. 12 can be implemented by hardware, software, firmware and/or any combination of hardware, software and/or firmware. Thus, for example, any of the example user input 1202, the example database 1204, the example display 1206, the example profile creator 1208, the example rules creator 1210, the example assignment manager 104, the example allocation manager 106, and/or, more generally, the example medical exam distributor 102 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example user input 1202, the example database 1204, the example display 1206, the example profile creator 1208, the example rules creator 1210, the example assignment manager 104, the example allocation manager 106, and/or, more generally, the example medical exam distributor 102 is/are hereby expressly defined to include a tangible computer readable storage device or storage disk such as a memory, a digital versatile disk (DVD), a compact disk (CD), a Blu-ray disk, etc. storing the software and/or firmware. Further still, the example medical exam distributor 102 of FIG. 12 can include one or more elements, processes and/or devices in addition to, or instead of, those illustrated in FIG. 12, and/or can include more than one of any or all of the illustrated elements, processes and devices.

Figure 13:
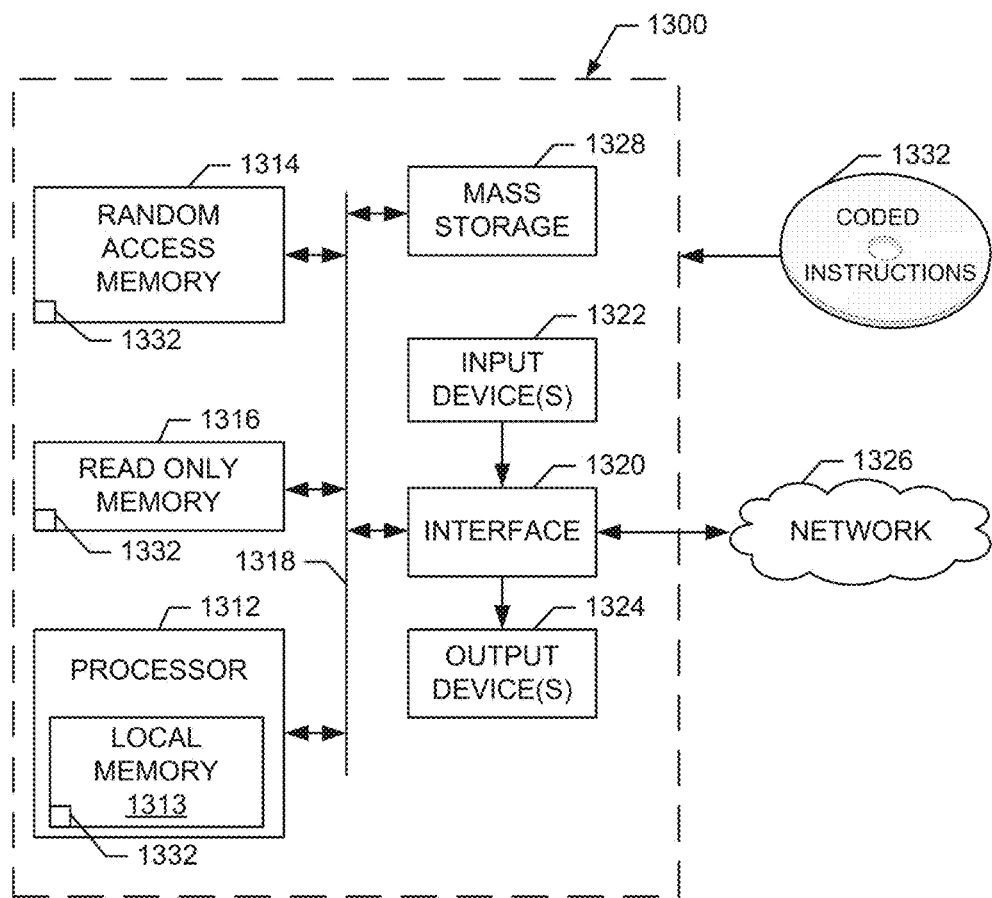
FIG. 13 shows a block diagram of an example processor system that may be used to implement systems and methods described herein.

FIG. 13 is a block diagram of an example processor platform 1300 capable of executing the instructions of FIGS. 3, 4, 5, 6, 7, 8, and/or 9 to implement the example medical exam distributor 102 of FIGS. 1, 2, and/or 10. The processor platform 1300 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 1300 of the illustrated example includes a processor 1312. The processor 1312 of the illustrated example is hardware. For example, the processor 1312 can be implemented by one or more integrated circuits, logic circuits, microprocessors or controllers from any desired family or manufacturer.

The processor 1312 of the illustrated example includes a local memory 1313 (e.g., a cache). The processor 1312 of the illustrated example is in communication with a main memory including a volatile memory 1314 and a non-volatile memory 1316 via a bus 1318. The volatile memory 1314 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1316 can be implemented by flash memory and/or any other desired type of memory device. Access to the main memory 1314, 1316 is controlled by a memory controller.

The processor platform 1300 of the illustrated example also includes an interface circuit 1320. The interface circuit 1320 can be implemented by any type of interface standard, such as an Ethernet interface, a universal serial bus (USB), and/or a PCI express interface.

In the illustrated example, one or more input devices 1322 are connected to the interface circuit 1320. The input device(s) 1322 permit(s) a user to enter data and commands into the processor 1312. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1324 are also connected to the interface circuit 1320 of the illustrated example. The output devices 1324 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 1320 of the illustrated example, thus, typically includes a graphics driver card, a graphics driver chip or a graphics driver processor.

The interface circuit 1320 of the illustrated example also includes a communication device such as a transmitter, a receiver, a transceiver, a modem and/or network interface card to facilitate exchange of data with external machines (e.g., computing devices of any kind) via a network 1326 (e.g., an Ethernet connection, a digital subscriber line (DSL), a telephone line, coaxial cable, a cellular telephone system, etc.).

The processor platform 1300 of the illustrated example also includes one or more mass storage devices 1328 for storing software and/or data. Examples of such mass storage devices 1328 include floppy disk drives, hard drive disks, compact disk drives, Blu-ray disk drives, RAID systems, and digital versatile disk (DVD) drives.

The coded instructions 1332 of FIGS. 3, 4, 5, 6, 7, 8, and/or 9 can be stored in the mass storage device 1328, in the volatile memory 1314, in the non-volatile memory 1316, and/or on a removable tangible computer readable storage medium such as a CD or DVD.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

The invention claimed is:

1. A method to allocate a medical exam, said method comprising:
   displaying, via a first graphical user interface, a first status indicator for the medical exam and a second status indicator for the medical exam, the first graphical user interface to be viewed by a plurality of radiologists;
   identifying, by executing an instruction using a processor, an exam characteristic associated with the medical exam;
   determining, by executing an instruction using the processor, a plurality of allocation scores for the plurality of radiologists by comparing the exam characteristic to a radiologist characteristic for each of the plurality of radiologists;

determining, by executing an instruction using the processor, one of the plurality of allocation scores with a highest value;

allocating, by executing an instruction using the processor, the medical exam to one of the plurality of radiologists associated with the one of the plurality of allocation scores with the highest value;

marking, via the first graphical user interface, the medical exam with the first status indicator as allocated to the one of the plurality of radiologists associated with the one of the plurality of allocation scores with the highest value;

distributing, by executing an instruction using the processor, the allocated medical exam to a work queue associated with the one of the plurality of radiologists associated with the one of the plurality of allocation scores with the highest value;

displaying, via a second graphical user interface, the work queue for viewing by the one of the plurality of radiologists associated with the one of the plurality of allocation scores with the highest value;

marking, via the first graphical user interface, the second status indicator based on a position of the allocated medical exam in the work queue;

monitoring, by executing an instruction with the processor, a status of a workstation associated with the one of the plurality of radiologists associated with the one of the plurality of allocation scores with the highest value for viewing the allocated medical exam;

automatically evaluating, by executing an instruction with the processor, the distribution of the medical exam if the workstation status satisfies a workstation activity threshold; and updating, via the first graphical user interface, at least one of the first status indicator or the second status indicator based on the evaluation.

2. The method of claim 1, wherein determining one of the plurality of allocation scores comprises:
assigning a specialty point value if a specialty associated with the medical exam matches a specialty associated with one of the plurality of radiologists;
assigning a modality point value if a modality associated with the medical exam matches a modality associated with the one of the plurality of radiologists;
assigning a body part point value if a body part associated with the medical exam matches a body part associated with the one of the plurality of radiologists; and
adding the specialty point value, the modality point value, and the body part point value.

3. The method of claim 1, wherein allocating the medical exam includes determining if the one of the plurality of radiologists associated with the one of the plurality of allocation scores with the highest value accepts the allocation of the medical exam.

4. The method of claim 3, further comprising adjusting a position of the medical exam in the work queue associated with the one of the plurality of radiologists associated with the one of the plurality of allocation scores with the highest value if the one of the plurality of radiologists associated with the one of the plurality of allocation scores with the highest value accepts the allocation of the medical exam.

5. The method of claim 1, wherein determining one of the plurality of allocation scores with a highest value includes determining a length of a work queue associated with each of the plurality of radiologists.

6. The method of claim 1, further comprising moving the medical exam to a first position of the work queue associated with the one of the plurality of radiologists associated with the one of the plurality of allocation scores with the highest value when a priority flag associated with the medical exam is set.

7. The method of claim 1, further comprising:
determining if an experience level of the one of the plurality of radiologists associated with the one of the plurality of allocation scores with the highest value is sufficient for a relative value unit score associated with the medical exam; and
deallocating the medical exam if the experience level is not sufficient.

8. A system to allocate a medical exam, said system comprising a processor, the processor configured to implement:
an allocation manager to:
display, via a first graphical user interface, a first status indicator for the medical exam and a second status indicator for the medical exam, the first graphical user interface to be viewed by a plurality of radiologists;
identify an exam characteristic associated with the medical exam;
determine a plurality of allocation scores for the plurality of radiologists by comparing the exam characteristic to a radiologist characteristic for each of the plurality of radiologists;
determine one of the plurality of allocation scores with a highest value;
allocate the medical exam to one of the plurality of radiologists associated with the one of the plurality of allocation scores with the highest value;
mark, via the first graphical user interface, the medical exam with the first status indicator as allocated to the one of the plurality of radiologists associated with the one of the plurality of allocation scores with the highest value;
distribute the allocated medical exam to a work queue of the one of the plurality of radiologists associated with the one of the plurality of allocation scores with the highest value;
display, via a second graphical user interface, the work queue for viewing by the one of the plurality of radiologists associated with the one of the plurality of allocation scores with the highest value;
mark, via the first graphical user interface, the second status indicator based on a position of the allocated medical exam in the work queue;
monitor a status of a workstation associated with the one of the plurality of radiologists associated with the one of the plurality of allocation scores with the highest value for viewing the allocated medical exam;
automatically evaluate the distribution of the medical exam if the workstation status satisfies a workstation activity threshold; and
update, via the first graphical user interface, at least one of the first status indicator or the second status indicator based on the evaluation.

9. The system of claim 8, wherein to determine one of the plurality of allocation scores, the allocation manager is to:

assign a specialty point value if a specialty associated with the medical exam matches a specialty associated with one of the plurality of radiologists;

assign a modality point value if a modality associated with the medical exam matches a modality associated with the one of the plurality of radiologists;

assign a body part point value if a body part associated with the medical exam matches a body part associated with the one of the plurality of radiologists; and add the specialty point value, the modality point value, and the body part point value.

10. The system of claim 8, wherein to allocate the medical exam, the allocation manager is to determine if the one of the plurality of radiologists associated with the one of the plurality of allocation scores with the highest value accepts the allocation of the medical exam.

11. The system of claim 10, wherein the allocation manager is to adjust a position of the medical exam in the work queue associated with the one of the plurality of radiologists associated with the one of the plurality of allocation scores with the highest value if the one of the plurality of radiologists associated with the one of the plurality of allocation scores with the highest value accepts the allocation of the medical exam.

12. The system of claim 8, wherein to determine one of the plurality of allocation scores with a highest value, the allocation manager is to determine a length of a work queue associated with each of the plurality of radiologists.

13. The system of claim 8, wherein the allocation manager is to further move the medical exam to a first position of a work queue associated with the one of the plurality of radiologists associated with the one of the plurality of allocation scores with the highest value when a priority flag associated with the medical exam is set.

14. The system of claim 8, wherein the allocation manager is to further:

determine if an experience level of the one of the plurality of radiologists associated with the one of the plurality of allocation scores with the highest value is sufficient for a relative value unit score associated with the medical exam; and deallocate the medical exam if the experience level is not sufficient.

15. A tangible computer readable storage medium comprising instructions that, when executed, cause a computing device to:

display, via a first graphical user interface, a first status indicator for a medical exam and a second status indicator for the medical exam, the first graphical user interface to be viewed by a plurality of radiologists;

identify an exam characteristic associated with the medical exam;

determine a plurality of allocation scores for a plurality of radiologists by comparing the exam characteristic to a radiologist characteristic for each of the plurality of radiologists;

determine one of the plurality of allocation scores with a highest value;

allocate the medical exam to one of the plurality of radiologists associated with the one of the plurality of allocation scores with the highest value;

mark, via the first graphical user interface, the medical exam with the first status indicator as allocated to the one of the plurality of radiologists associated with the one of the plurality of allocation scores with the highest value;

distribute the allocated medical exam to a work queue associated with the one of the plurality of radiologists associated with the one of the plurality of allocation scores with the highest value;

display, via a second graphical user interface, the work queue for viewing by the one of the plurality of radiologists associated with the one of the plurality of allocation scores with the highest value;

mark, via the first graphical user interface, the second status indicator based on a position of the allocated medical exam in the work queue;

monitor a status of a workstation associated with the one of the plurality of radiologists associated with the one of the plurality of allocation scores with the highest value for viewing the allocated medical exam;

automatically evaluate the distribution of the medical exam if the workstation status satisfies a workstation activity threshold; and update at least one of the first status indicator or the second status indicator based on the evaluation.

16. The tangible computer readable storage medium of claim 15, wherein determining one of the plurality of allocation scores comprises:

assigning a specialty point value if a specialty associated with the medical exam matches a specialty associated with one of the plurality of radiologists;

assigning a modality point value if a modality associated with the medical exam matches a modality associated with the one of the plurality of radiologists;

assigning a body part point value if a body part associated with the medical exam matches a body part associated with the one of the plurality of radiologists; and adding the specialty point value, the modality point value, and the body part point value.

17. The tangible computer readable storage medium of claim 15, wherein allocating the medical exam includes determining if the one of the plurality of radiologists associated with the one of the plurality of allocation scores with the highest value accepts the allocation of the medical exam.

18. The tangible computer readable storage medium of claim 17, further comprising instructions that, when executed, cause the computing device to adjust a position of the medical exam in the work queue associated with the one of the plurality of radiologists associated with the one of the plurality of allocation scores with the highest value if the one of the plurality of radiologists associated with the one of the plurality of allocation scores with the highest value accepts the allocation of the medical exam.

19. The tangible computer readable storage medium of claim 15, wherein determining one of the plurality of allocation scores with a highest value includes determining a length of a work queue associated with each of the plurality of radiologists.

20. The tangible computer readable storage medium of claim 15, further comprising instructions that, when executed, cause the computing device to move the medical exam to a first position of the work queue associated with the one of the plurality of radiologists associated with the one of the plurality of allocation scores with the highest value when a priority flag associated with the medical exam is set.

21. The method of claim 1, wherein the workstation activity threshold is indicative of an idle state of the workstation.

* * * * *